US011466244B2

(12) United States Patent
Ananta et al.

(10) Patent No.: US 11,466,244 B2
(45) Date of Patent: Oct. 11, 2022

(54) COMPOSITION SUITABLE FOR PROTECTING MICROORGANISMS

(71) Applicant: SOCIÉTÉ DES PRODUITS NESTLÉ S.A., Vevey (CH)

(72) Inventors: Edwin Ananta, Epalinges (CH); Biljana Bogicevic, Bern (CH); Carsten Cramer, Grosshochstetten (CH); Alexandra Dubois, Bodenheim (DE); Judith Gaulocher, Strengelbach (CH); Katja Johnson, Konolfingen (CH); Jeroen Andre Muller, Singapore (SG); Matthias Perren, Brugg (CH); Guenolee Eliane Marie Prioult, Bern (CH); Sabine Sres, Oberdiessbach (CH); Wilbert Sybesma, Munsingen (CH)

(73) Assignee: Societe des Produits Nestle S.A., Vevey (CH)

( * ) Notice: Subject to any disclaimer, the term of this patent is extended or adjusted under 35 U.S.C. 154(b) by 64 days.

(21) Appl. No.: 16/897,798

(22) Filed: Jun. 10, 2020

(65) Prior Publication Data
US 2020/0299633 A1     Sep. 24, 2020

Related U.S. Application Data

(62) Division of application No. 15/580,804, filed as application No. PCT/EP2016/065359 on Jun. 30, 2016, now Pat. No. 10,711,240.

(30) Foreign Application Priority Data

Jun. 30, 2015   (EP) ..................... 15174488

(51) Int. Cl.
C12N 1/04      (2006.01)
C12N 1/20      (2006.01)

(52) U.S. Cl.
CPC ...... *C12N 1/04* (2013.01); *C12N 1/20* (2013.01)

(58) Field of Classification Search
CPC ................... C12N 1/04; C12N 1/20
See application file for complete search history.

(56) References Cited

U.S. PATENT DOCUMENTS 6,010,725 A     1/2000   Meister et al.
6,641,808 B1   11/2003   Bojrab et al.
2003/0138936 A1 *  7/2003  Mizuguchi .......... A23L 29/065
                                                  435/252.31
2003/0215515 A1 * 11/2003  Truong-Le .......... A61P 37/04
                                                  424/489
2004/0191392 A1    9/2004  Hung et al.
2005/0100559 A1 *  5/2005  Myatt .................. A61P 43/00
                                                  424/234.1
2007/0072293 A1    3/2007  Kole et al.
2009/0087418 A1    4/2009  Strozzi et al.
2011/0223136 A1    9/2011  Schiffrin et al.
2013/0337108 A1 * 12/2013  Van Hee ............ A23C 9/1238
                                                  426/11
2014/0065219 A1    3/2014  Bosch et al.

FOREIGN PATENT DOCUMENTS

EP   1281752      2/2003
EP   1867713     12/2007
EP   2517699     10/2012
WO   2004101758  11/2004
WO   2012077038   6/2012

OTHER PUBLICATIONS

Germani et al., "The Yogurt Amino Acid Profile's Variation During the Shelf-life", Ann ig, vol. 26, May 1, 2014, pp. 205-212, XP55626806.
Abd-Talib et al., Agric. Sci., 4(5B):78-83 (2013) (Year: 2013).
Behboudi-Jobbehdar et al., Drying Tech., 31: 11, 127 4-1283 (2013) (Year: 2013).
Menshutina et al., Drying Tech., 28(10):1170-1177 (2010) (Year: 2010).
Leja et al., Acta Sci. Pol., Technol. Aliment., 8(4):39-49 (2009) (Year: 2009).
Shokri et al., DARU J. Pharma. Sci., 23(7): 1-9 (2015) (Year: 2015).
Soukoulis et al., Food Bioprocess Technol., 7: 1255-1268 (2014) (Year: 2014).
Yonekura et al., J. Funct. Foods, 6:205-214 (2014) (Year: 2014).
Golowczyc et al., Biotechnol. Let. 33(4):681-686 (2011) (Year: 2011).

* cited by examiner

*Primary Examiner* — Louise W Humphrey
*Assistant Examiner* — Trevor L Kane
(74) *Attorney, Agent, or Firm* — K&L Gates LLP

(57) ABSTRACT

A composition includes at least one carrier containing a polysaccharide, at least one antioxidant and at least one amino acid selected from cysteine, lysine, alanine and arginine. Such a composition can be used for protection of microorganisms during drying, storage and/or reconstitution. A culture powder, a process of making the culture powder, and products containing the culture powder are also disclosed.

11 Claims, 17 Drawing Sheets

COMPOSITION SUITABLE FOR PROTECTING MICROORGANISMS

CROSS REFERENCE TO RELATED APPLICATIONS

The present application is a divisional of U.S. patent application Ser. No. 15/580,804 filed on Dec. 8, 2017, which is a National Stage of International Application No. PCT/EP2016/065359 filed on Jun. 30, 2016, which claims priority to European Patent Application No. 15174488.5 filed on Jun. 30, 2015, the entire contents of which are being incorporated herein by reference.

TECHNICAL FIELD

The present invention relates to a composition comprising at least one carrier comprising a polysaccharide, at least one antioxidant and at least one amino acid selected from cysteine, lysine, alanine and arginine. It also relates to the use of such a composition for the protection of microorganisms during drying, storage and/or reconstitution, to a culture powder, to a process of making the culture powder and to products comprising the culture powder.

BACKGROUND

Beneficial culture powders and in particular probiotic culture powders are added to a wide range of shelf-stable products. Most low moisture products containing probiotic culture powders claim a shelf-life of at least 18 months. During this period, a minimum amount of live microbes must be guaranteed in the product. For this reason, the dosage of culture powder in the product needs to account for the loss in microbial viability during storage. It is therefore important to find ways of protecting microorganisms during processing and during storage to promote their survival.

Bacteria experience various stresses during drying under warm conditions, such as heat and shear stress in the dryer or osmotic stress due to dehydration, for example during spray-drying. These stresses can have detrimental or even lethal effects on the bacteria. By addition of protective agents, the bacteria can be stabilized to a certain degree against these stresses. Further stress is applied on the bacteria during storage. Also, when the powder is reconstituted with liquid, the bacteria are exposed to osmotic stress.

Protective agents can stabilize microorganisms during drying, storage and/or reconstitution. A protective effect during drying mostly comes along with a stabilizing effect during storage and reconstitution, because when microorganisms are better protected during drying, they are less injured and, as a consequence, more robust during storage and reconstitution.

Numerous ingredients have been suggested in literature as protective agents. For example, JP3504365 describes a protective agent for freeze-drying of bacteria comprising a mixture of at least three ingredients selected from aspartic acid, arginine, glutamic acid, proline, lysine, leucine and methionine. However, freeze-drying and drying processes using warm gas, such as spray-drying, are very different in nature and expose the biomass to different stress factors. Therefore disclosed protective agents for freeze-drying processes are of no help to identify protective agents suitable to protect microorganisms such as bacteria during a drying process using a warm gas, such as spray-drying, and subsequent storage and reconstitution.

Some documents relate specifically to the spray-drying of microorganisms. For example EP1281752 B1 describes a method of spray-drying microbial cells. Focus is on the size of the powder particles obtained and on the low temperature used for the drying process. This document also states that a protective agent commonly known in the art can be used. It provides numerous examples of potential protective agents, namely vitamins such as ascorbic acid; amino acids such as glutamine, glutamic acid, cysteine, glycine, phenylalanine, serine or threonine; saccharides or sugar alcohols such as glucose, fructose, sucrose, maltose, mannitol or maltitol; polysaccharides such as oligosaccharides, cyclodextrin or dextrin; fats such as higher fatty acids obtained from rapeseed, soybean, peanut, etc.; proteins such as those obtained from cow's milk, soybean, etc. and degraded proteins such as peptides; inorganic salts such as magnesium sulphate; and others such as sucrose fatty acid ester, malic acid, nucleic acids, yeast extract, skim milk, peptone, gelatin, tannin, etc. These ingredients can be used alone or in any combination thereof. This document does not provide any guidance with regards to selection of particular combinations of ingredients having optimal activity.

Similarly U.S. Pat. No. 6,010,725 relates to spray-drying of microorganisms and their survival. Its teaching is focused on the conditions to be applied during the spray-drying process. It also states that a variety of protective agents known in the literature can be used and recites as examples ascorbic acid, amino acids and their salts such as lysine, cysteine, glycine and sodium glutamate, proteins or protein hydrolysates, sugars such as lactose, trehalose, sucrose, dextrin and maltodextrin, and fats.

Despite the numerous disclosures of abundant lists of ingredients of potential use as protective agents, there is a need for further refinement and identification of combinations of ingredients having optimized activity to protect microorganisms during drying processes using warm gas and along subsequent storage and reconstitution.

The present invention advantageously solves the above-mentioned problems.

SUMMARY

In a first aspect, the invention provides a composition comprising a carrier material comprising a polysaccharide, at least one antioxidant and at least one amino acid selected from lysine, alanine, cysteine and arginine.

In a second aspect, the invention provides for the use of a composition according to the invention for the protection of microorganisms during a drying process using warm gas, during storage and/or during reconstitution.

In a third aspect, the invention provides a culture powder comprising live microorganisms and a matrix comprising a composition according to the present invention, the matrix: live microorganism dry weight ratio being of at least 1.

In a fourth aspect, the invention provides a process for preparing a culture powder comprising producing a biomass by fermentation with a microorganism;

concentrating the biomass obtained in step a);

conditioning the concentrated biomass with an aqueous solution of a composition according to the invention; and drying the conditioned biomass with warm gas to form a powder.

In a fifth aspect, the invention provides a product comprising a culture powder according to the invention.

Figure 2:
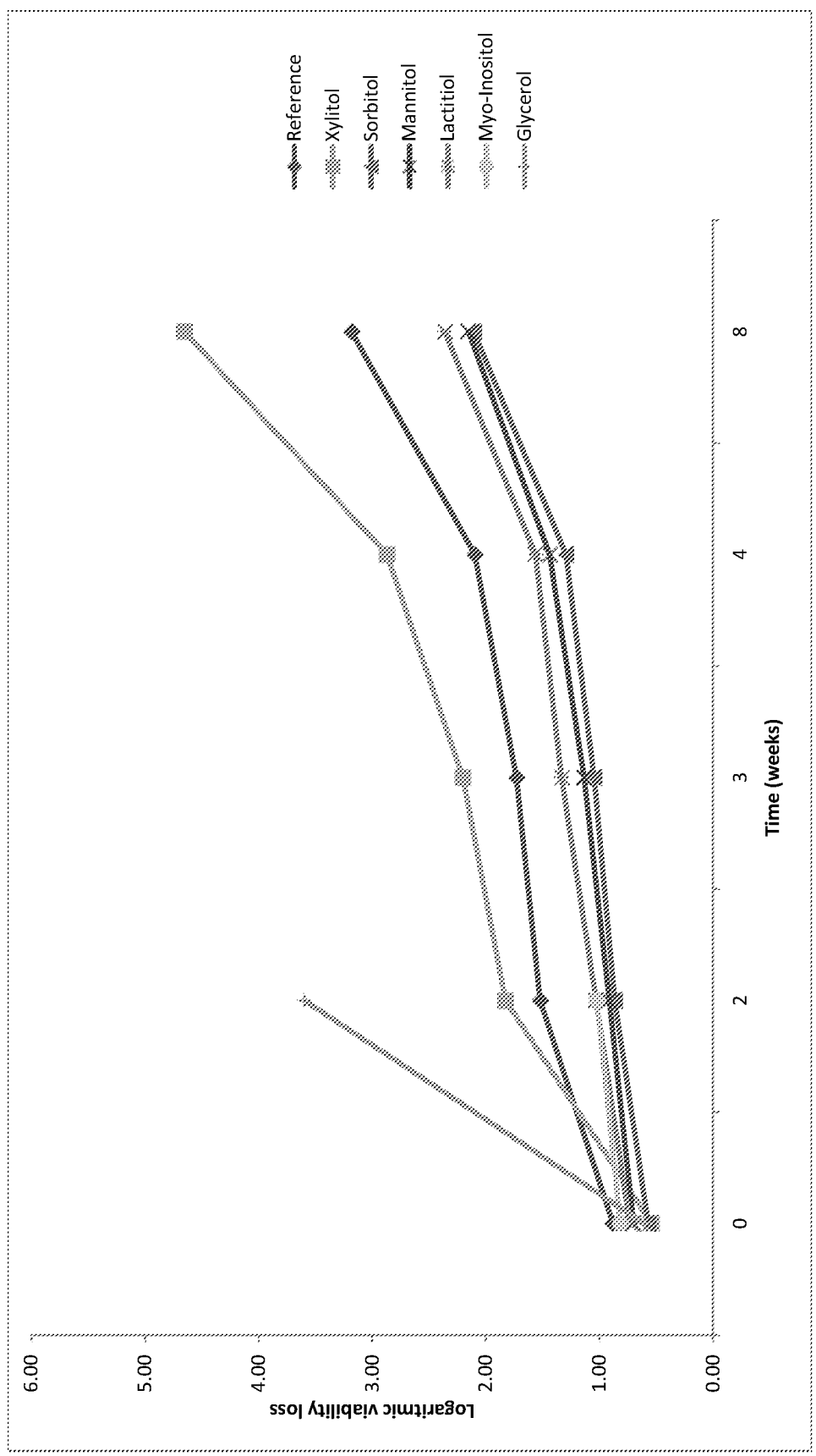

FIG. 2: Logarithmic viability loss of *B. longum* BL999 after spray-drying and after 2, 4, 6 and 8 weeks storage with xylitol, sorbitol, mannitol, lactitol, myo-inositol or glycerol as protective agent, as measured in the pre-screening trial of Example 1.

Figure 3:
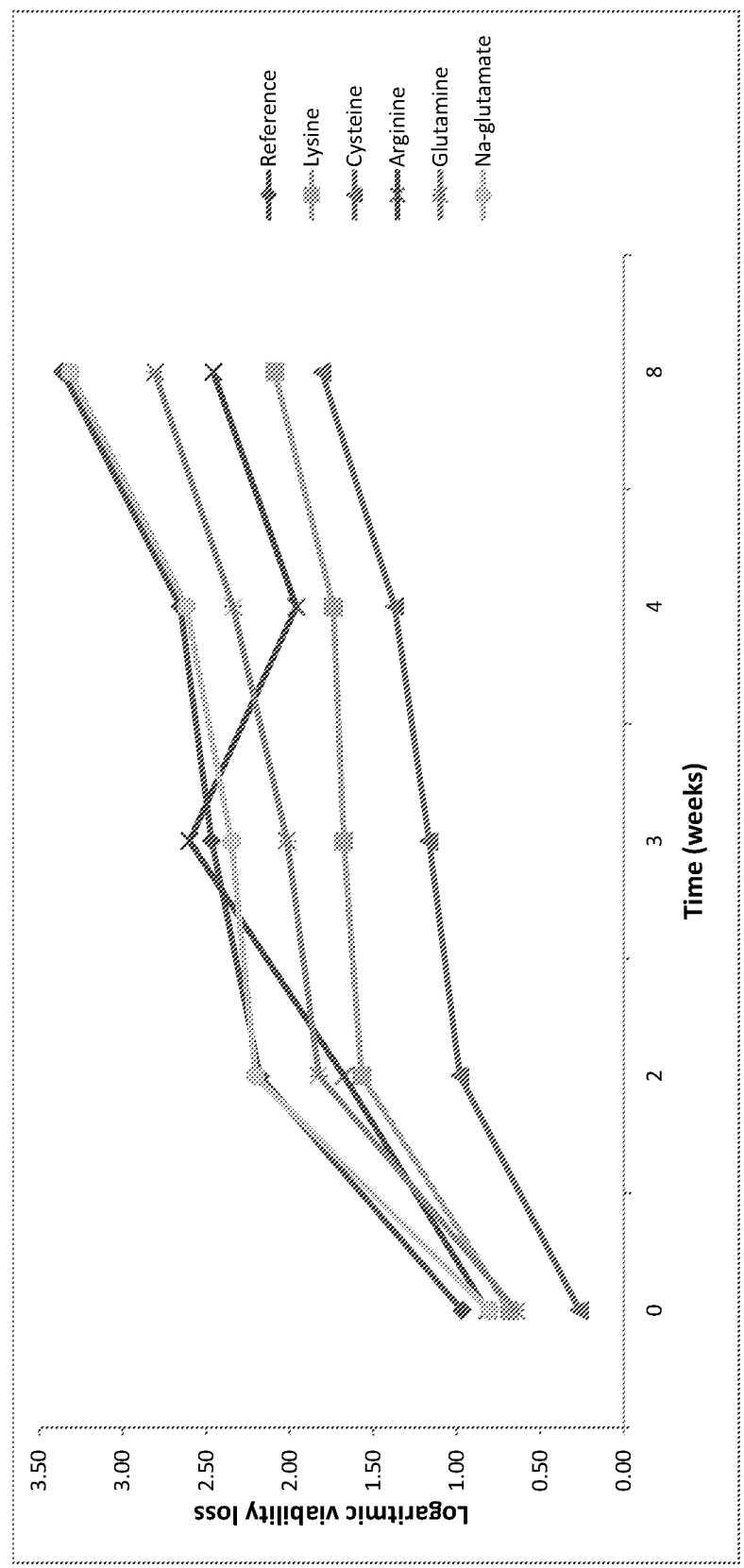

FIG. 3: Logarithmic viability loss of *B. longum* BL999 after spray-drying and after 2, 4, 6 and 8 weeks storage with sodium glutamate, glutamine, arginine, alanine, lysine or cysteine as protective agent, as measured in the pre-screening trial of Example 1.

Figure 4:
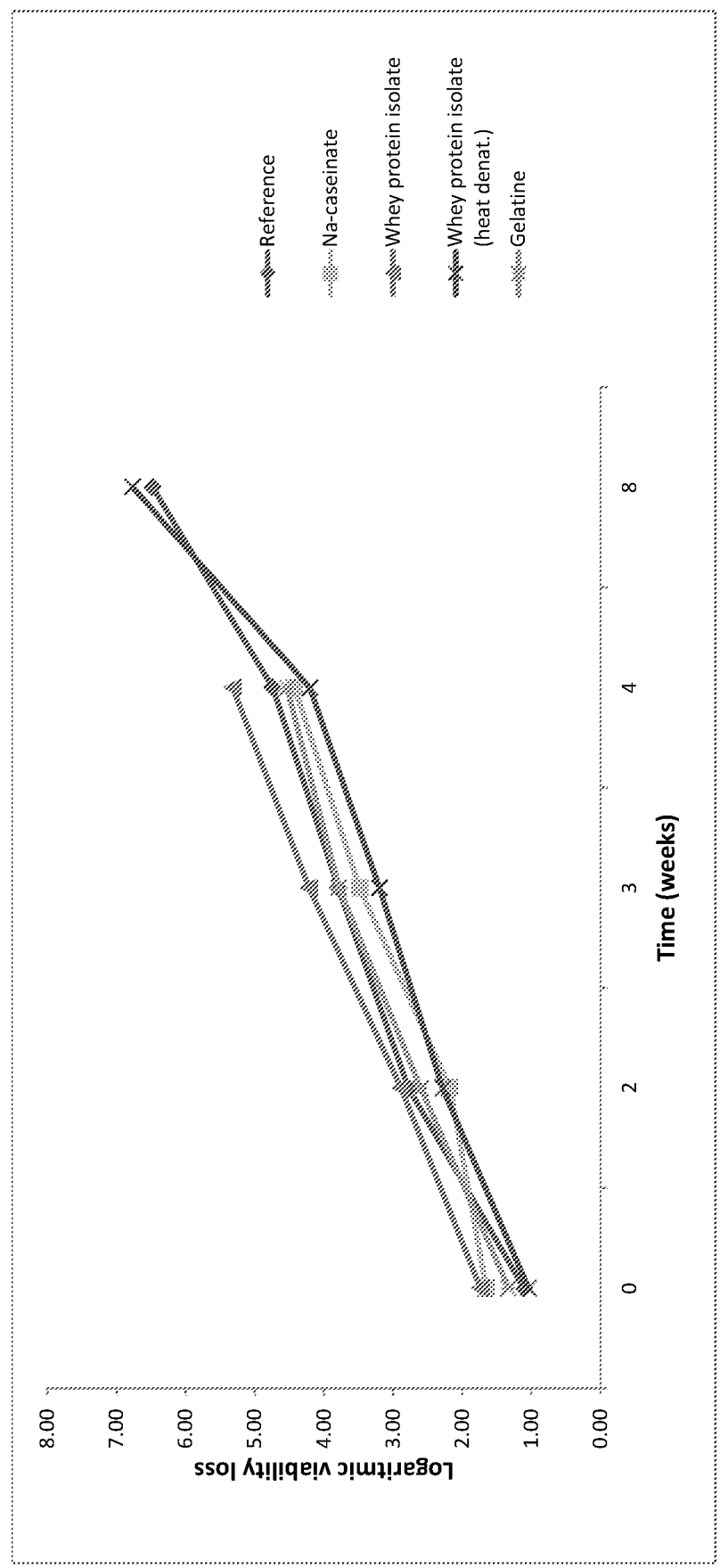

FIG. 4: Logarithmic viability loss of *B. longum* BL999 after spray-drying and after 2, 4, 6 and 8 weeks storage with sodium caseinate, whey protein isolate, heat denaturated whey protein isolate or gelatin as protective agent, as measured in the pre-screening trial of Example 1.

Figure 5:
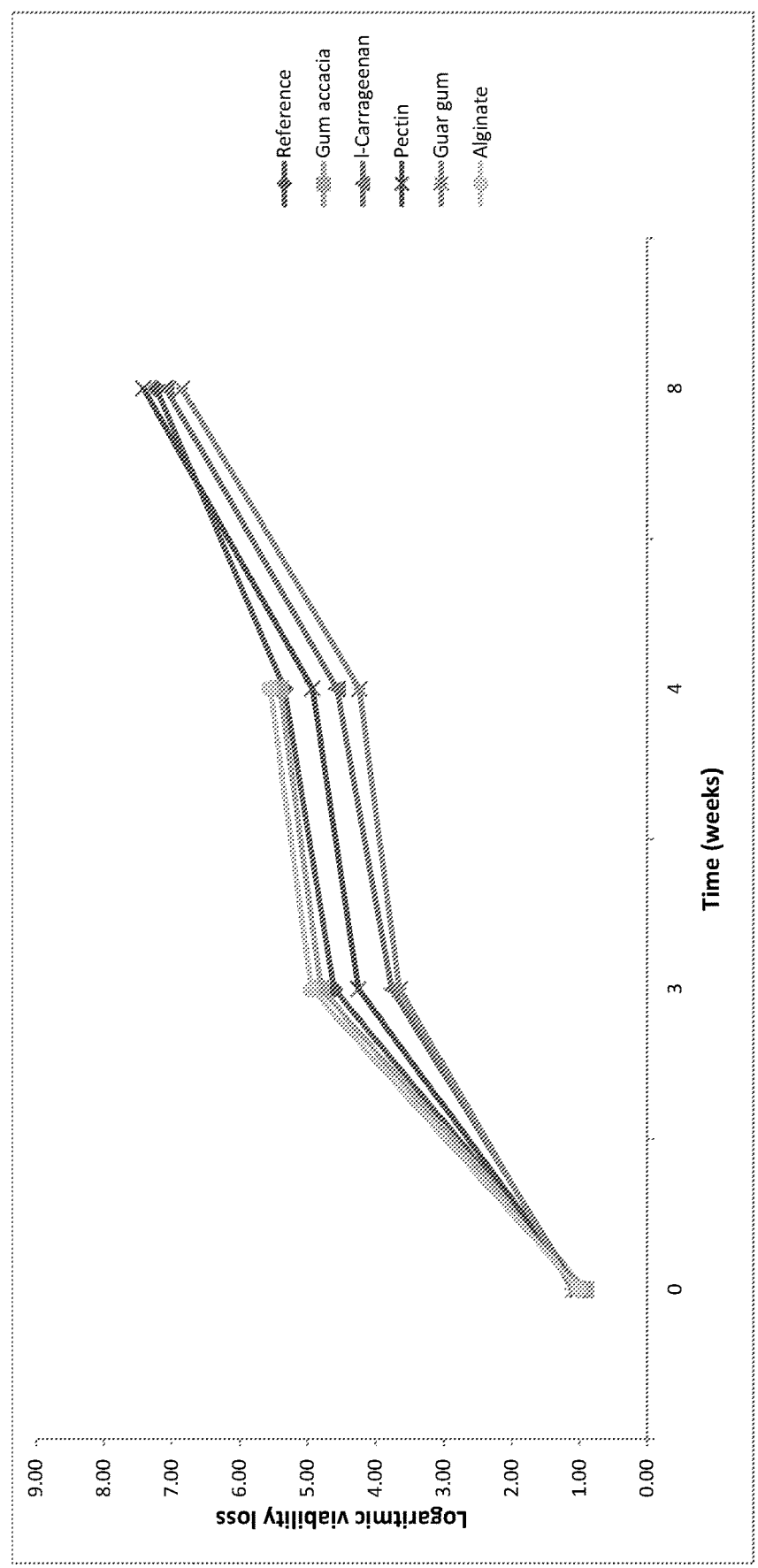

FIG. 5: Logarithmic viability loss of *B. longum* BL999 after spray-drying and after 2, 4, 6, 8, and 12 weeks storage with gum acacia, A-carrageenan, pectin, guar gum or alginate as protective agent, as measured in the pre-screening trial of Example 1.

Figure 6:
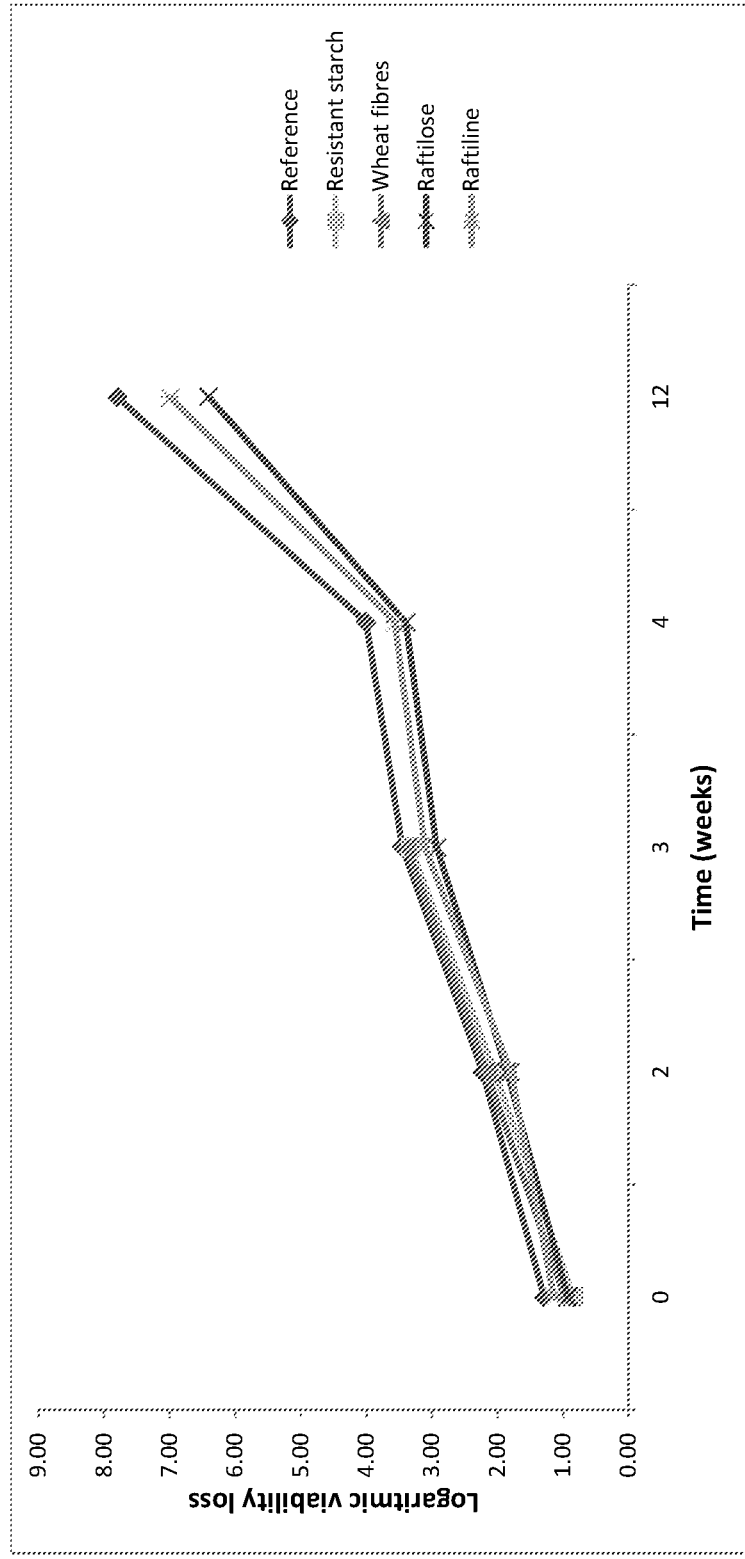

FIG. 6: Logarithmic viability loss of *B. longum* BL999 after spray-drying and after 2, 4, 6, 8, and 12 weeks storage with resistant starch, wheat fibres, raftilose or raftiline as protective agent, as measured in the pre-screening trial of Example 1.

Figure 7:
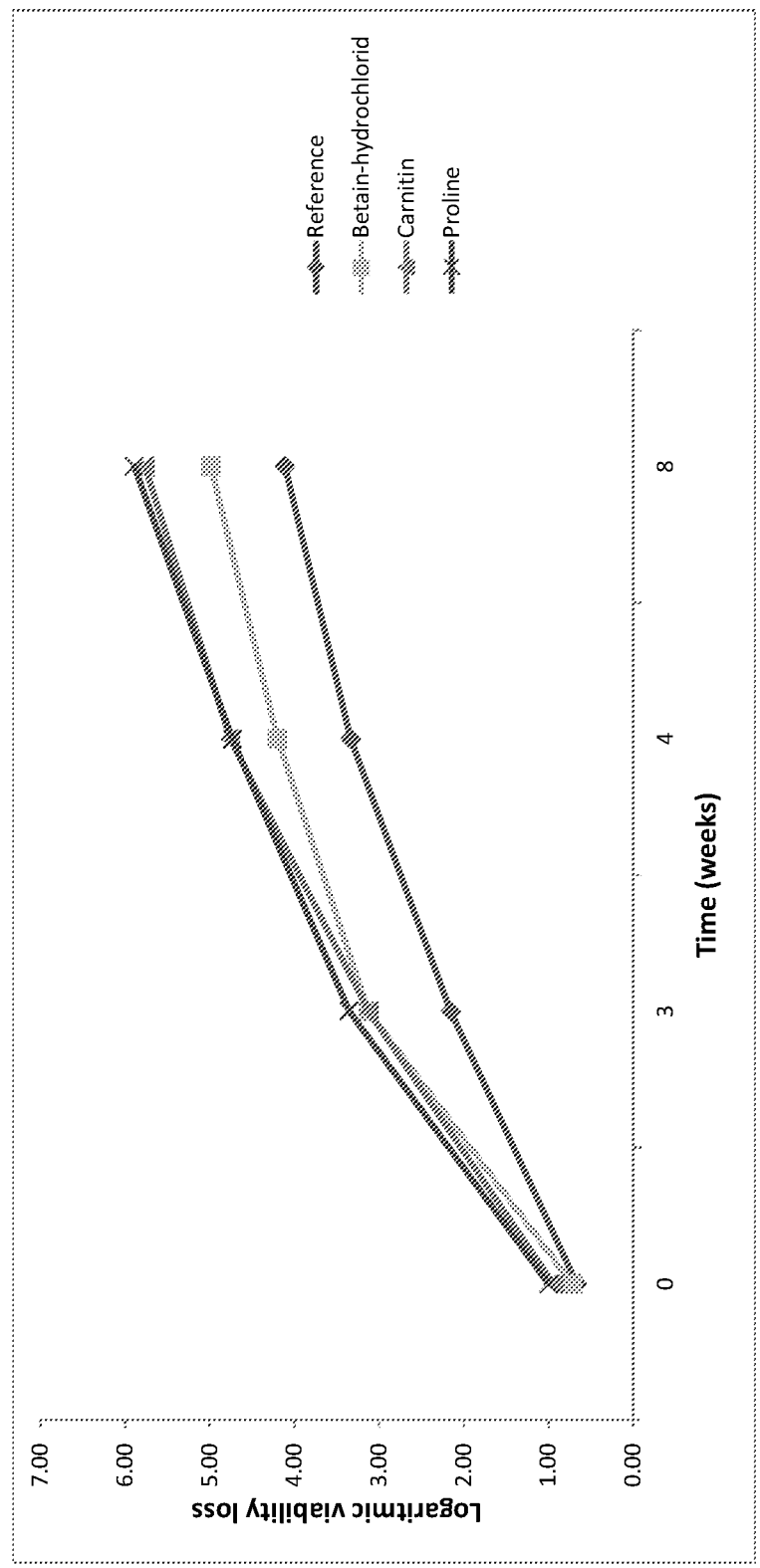

FIG. 7 Logarithmic viability loss of *B. longum* BL999 after spray-drying and after 2, 4, 6, 8, and 12 weeks storage with betain HCL, carnitine or proline as protective agent, as measured in the pre-screening trial of Example 1.

Figure 8:
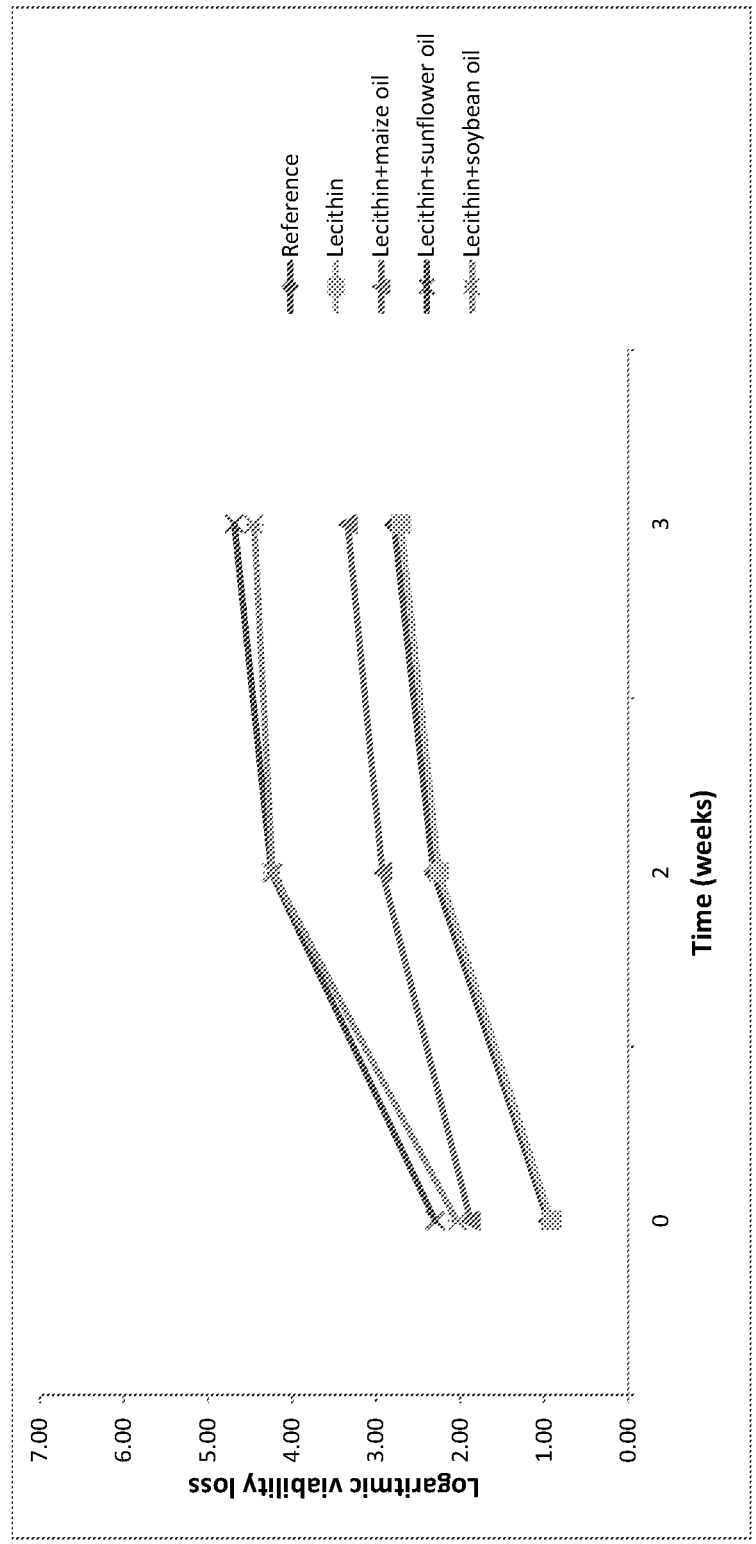

FIG. 8: Logarithmic viability loss of *B. longum* BL999 after spray-drying and after 2, and 3 weeks storage with lecithin, a mixture of lecithin and maize oil, a mixture of lecithin and sunflower oil or a mixture of lecithin and soybean oil as protective agent, as measured in the pre-screening trial of Example 1.

Figure 9:
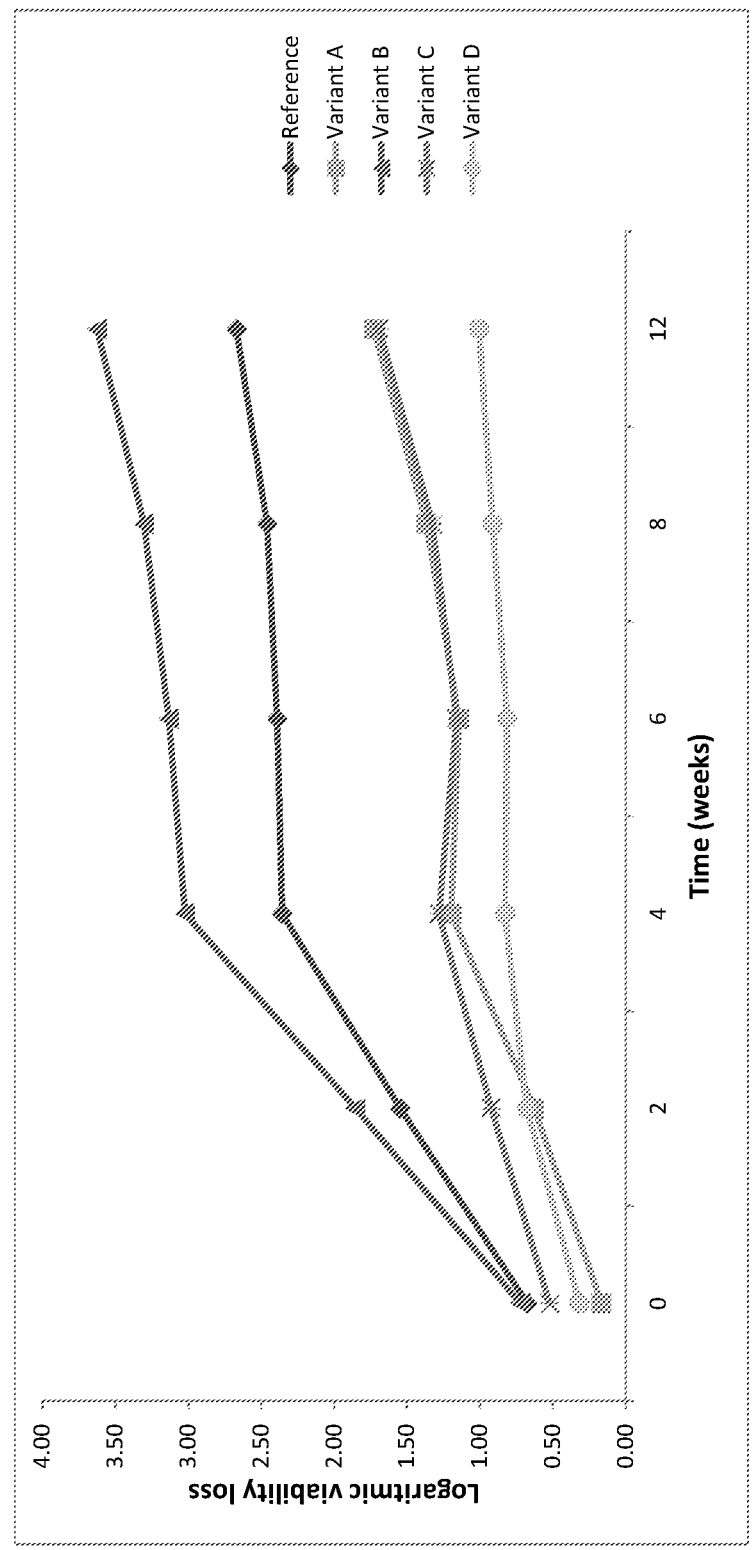

FIG. 9: Logarithmic viability loss of *B. longum* BL999 after spray-drying and after 2, 4, 6, 8 and 12 weeks storage with Variants A to D and the Reference as protective agent, as measured in the trial with combinations of ingredients in Example 1.

Figure 10:
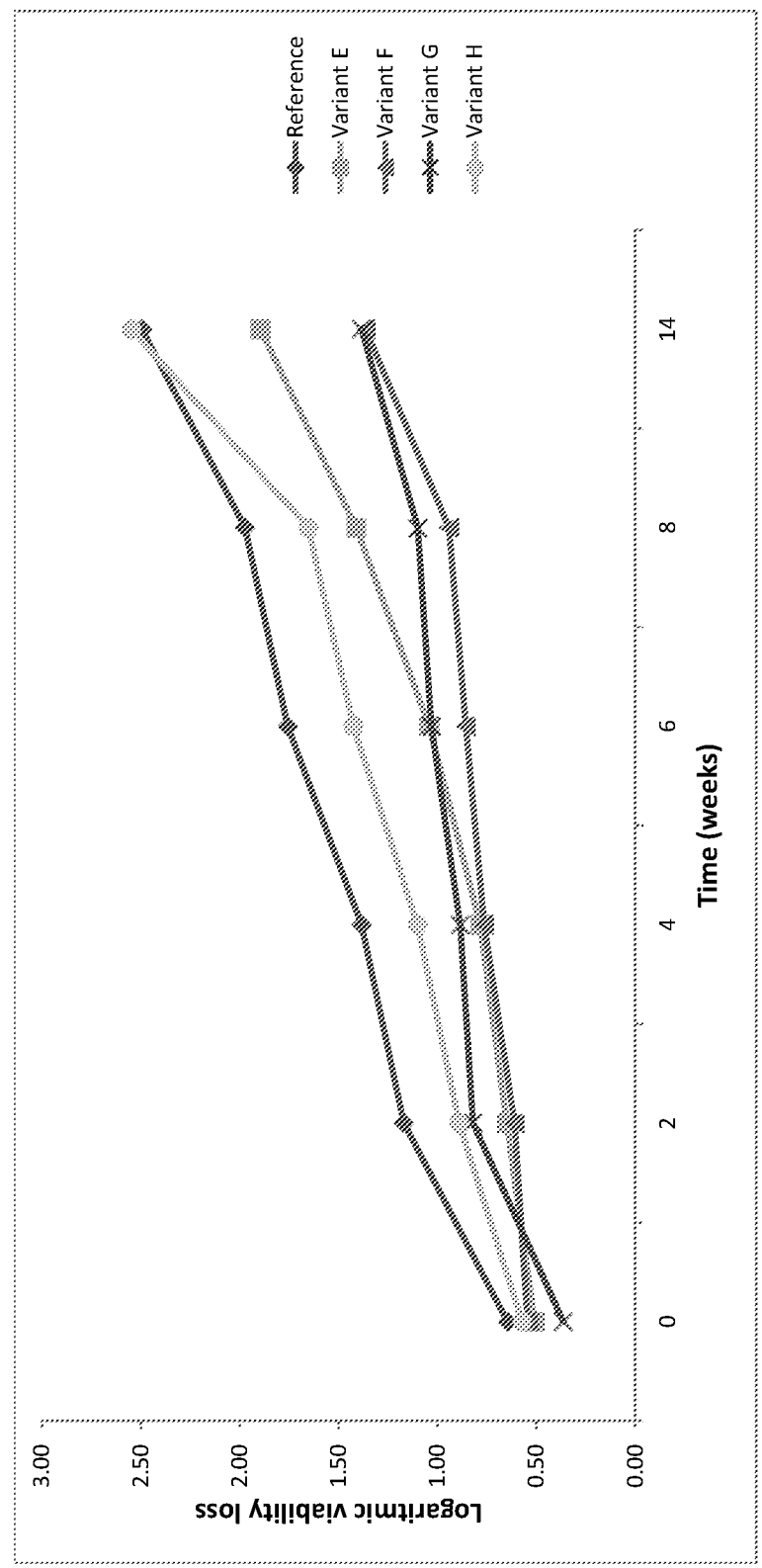

FIG. 10: Logarithmic viability loss of *B. longum* BL999 after spray-drying and after 2, 4, 6, 8 and 12 weeks storage with Variants E to H and the Reference as protective agent, as measured in the trial with combinations of ingredients in Example 1.

Figure 11:
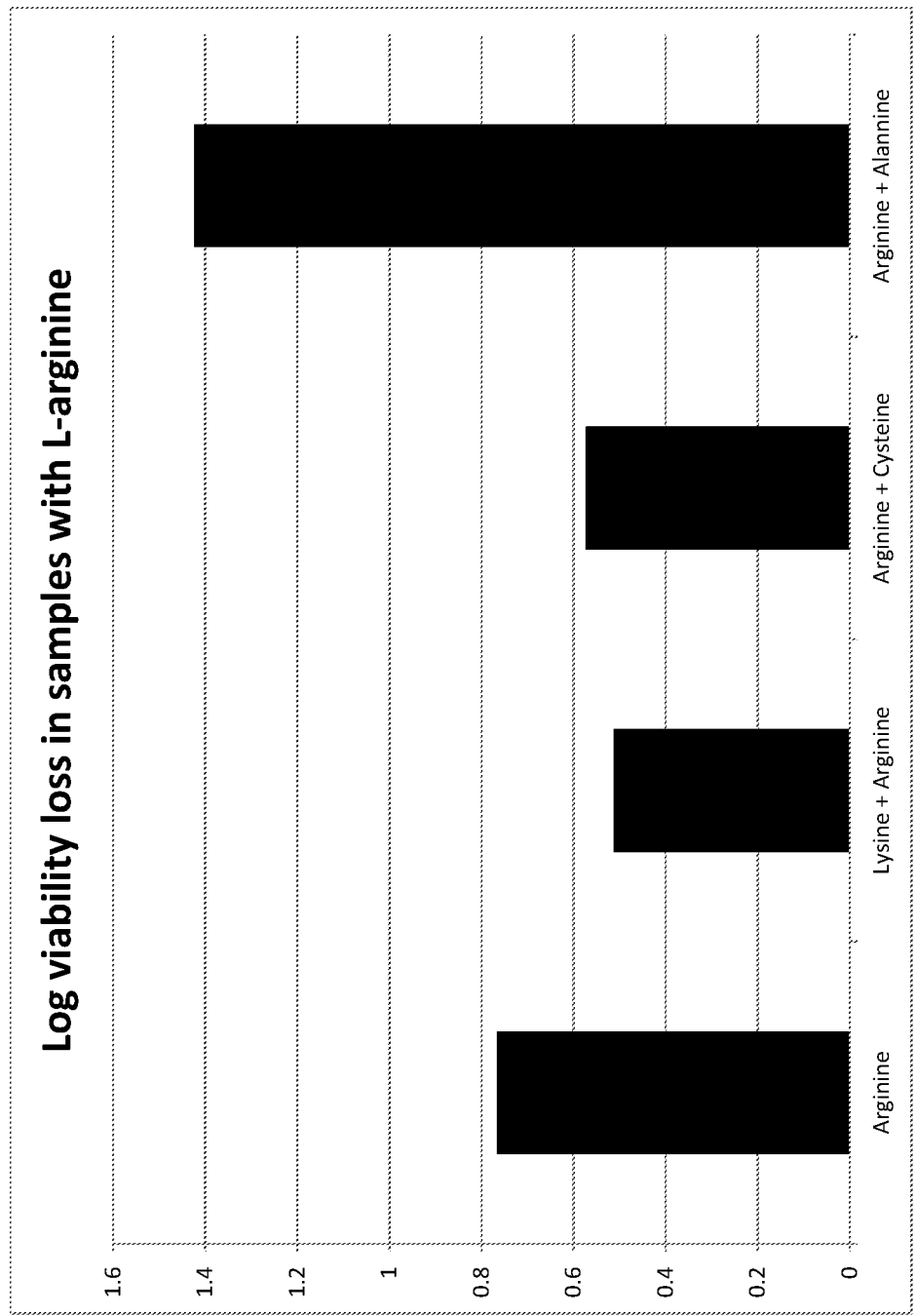

FIG. 11: Logarithmic viability loss of *B. longum* BL999 after 8 weeks storage after air convective drying in Samples 1, 5, 6 and 7 (all comprising L-lysine, either alone or in pair with one other amino acid selected from L-cysteine, L-alanine and L-arginine), as measured in Example 2.

Figure 12:
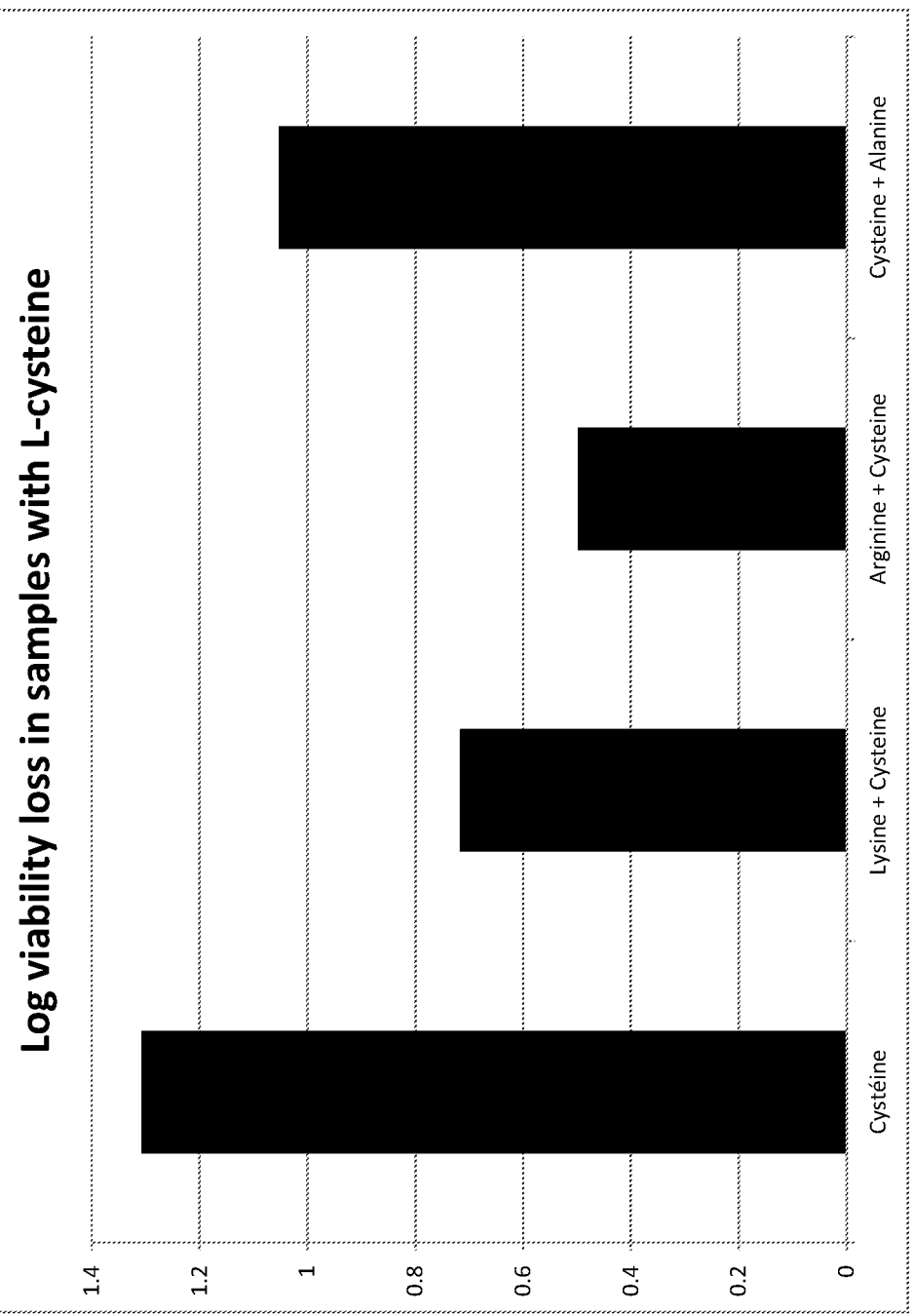

FIG. 12: Logarithmic viability loss of *B. longum* BL999 after 8 weeks storage after air convective drying in Samples 2, 5, 8 and 9 (all comprising L-arginine, either alone or in pair with one other amino acid selected from L-cysteine, L-alanine and L-lysine), as measured in Example 2.

Figure 13:
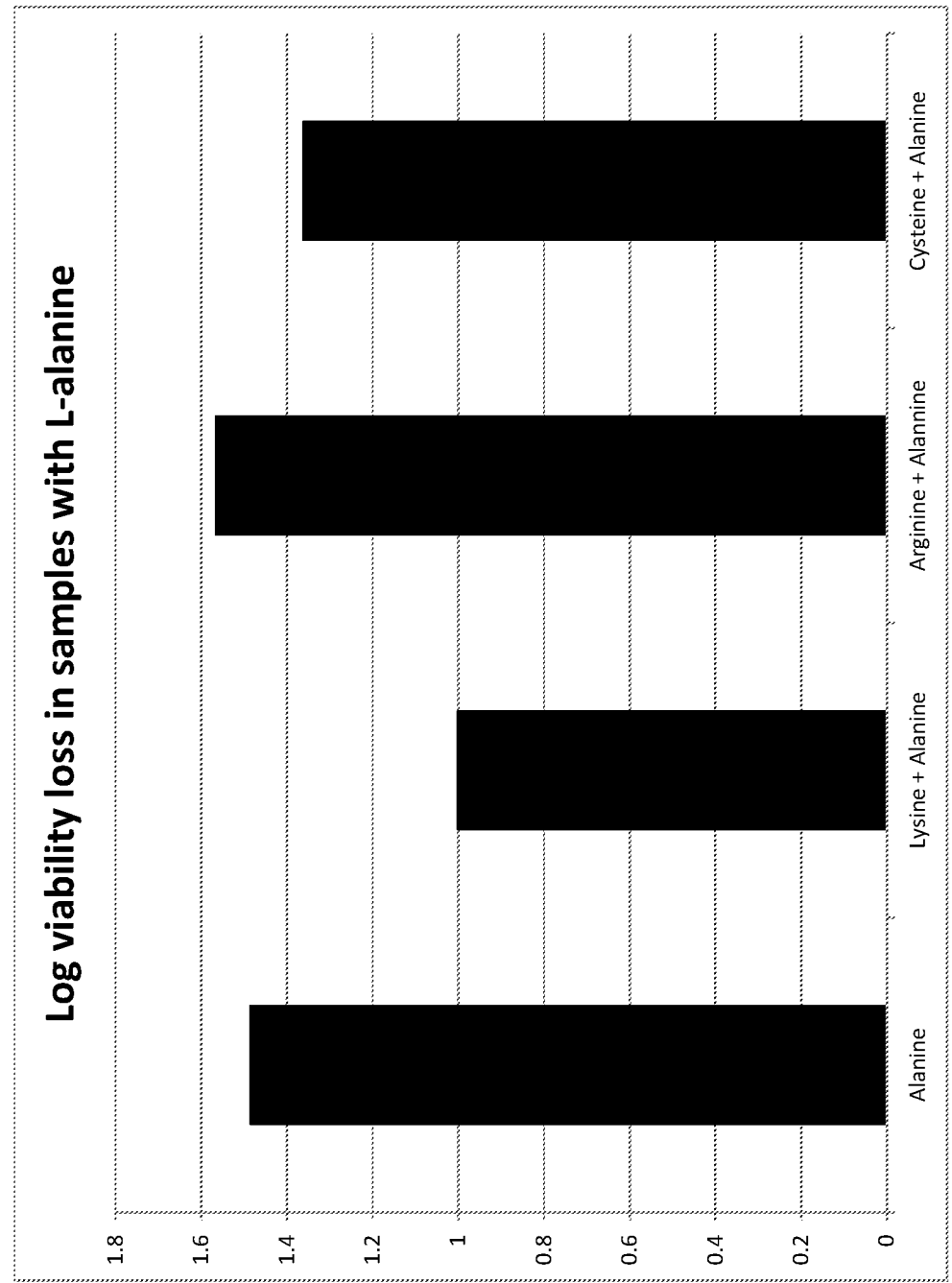

FIG. 13: Logarithmic viability loss of *B. longum* BL999 after 8 weeks storage after air convective drying in Samples 3, 6, 8 and 10 (all comprising L-cysteine, either alone or in pair with one other amino acid selected from L-arginine, L-alanine and L-lysine), as measured in Example 2.

Figure 14:
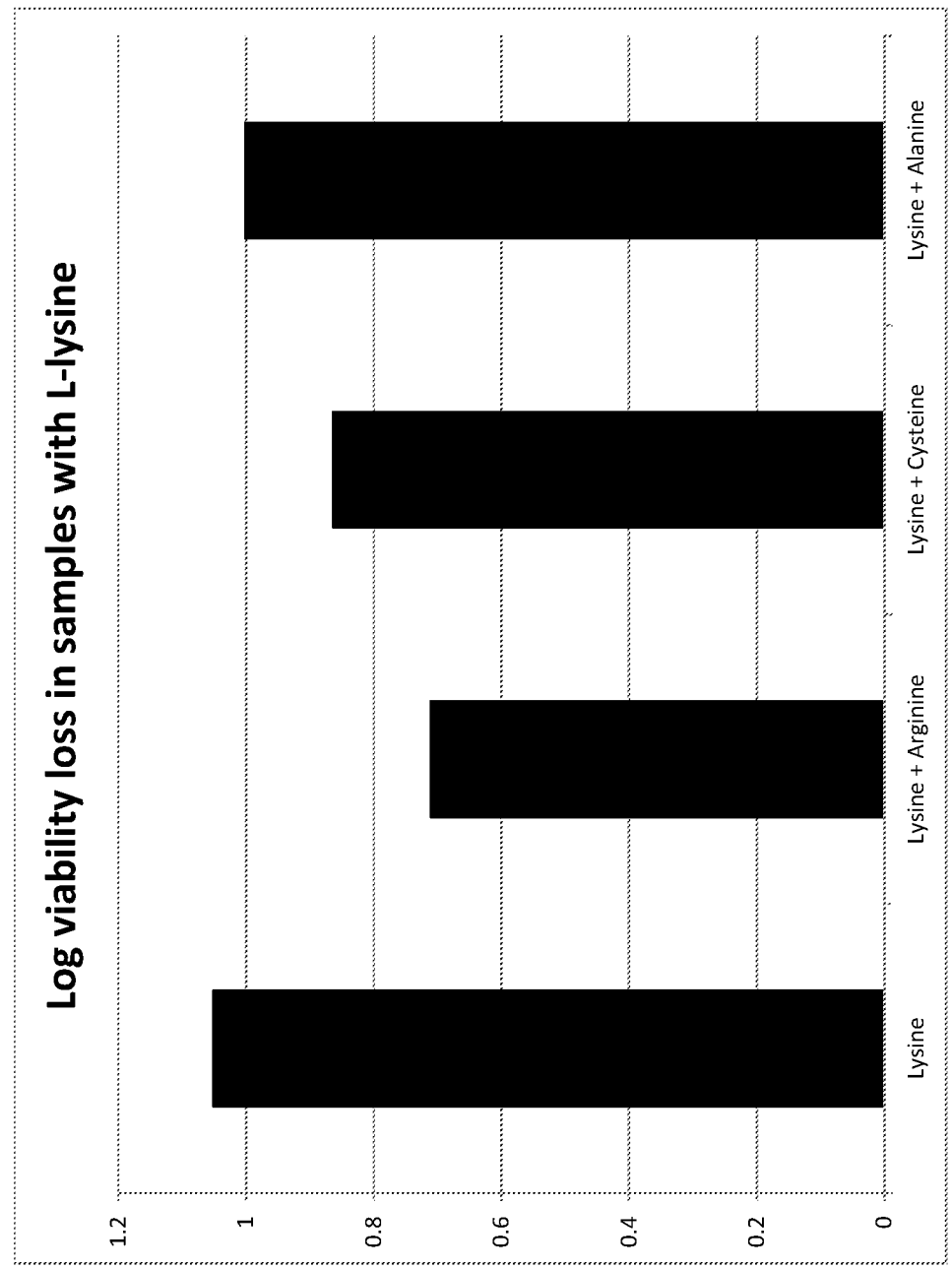

FIG. 14: Logarithmic viability loss of *B. longum* BL999 after 8 weeks storage after air convective drying in Samples 4, 7, 9 and 10 (all comprising L-alanine, either alone or in pair with one other amino acid selected from L-cysteine, L-arginine and L-lysine), as measured in Example 2.

Figure 15:
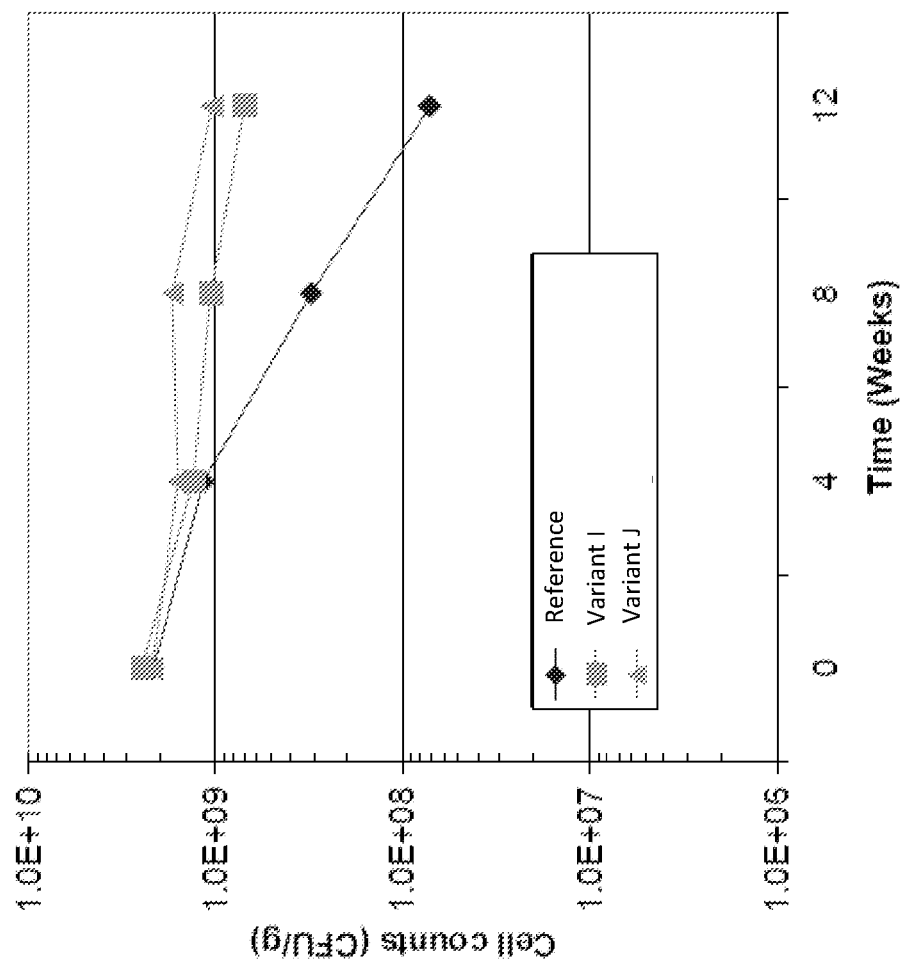

FIG. 15: Cell counts of *Streptococcus thermophilus* ST496 after 4, 8 and 12 weeks storage in Variants I and J and in the Reference, as measured in Example 3.

Figure 16:
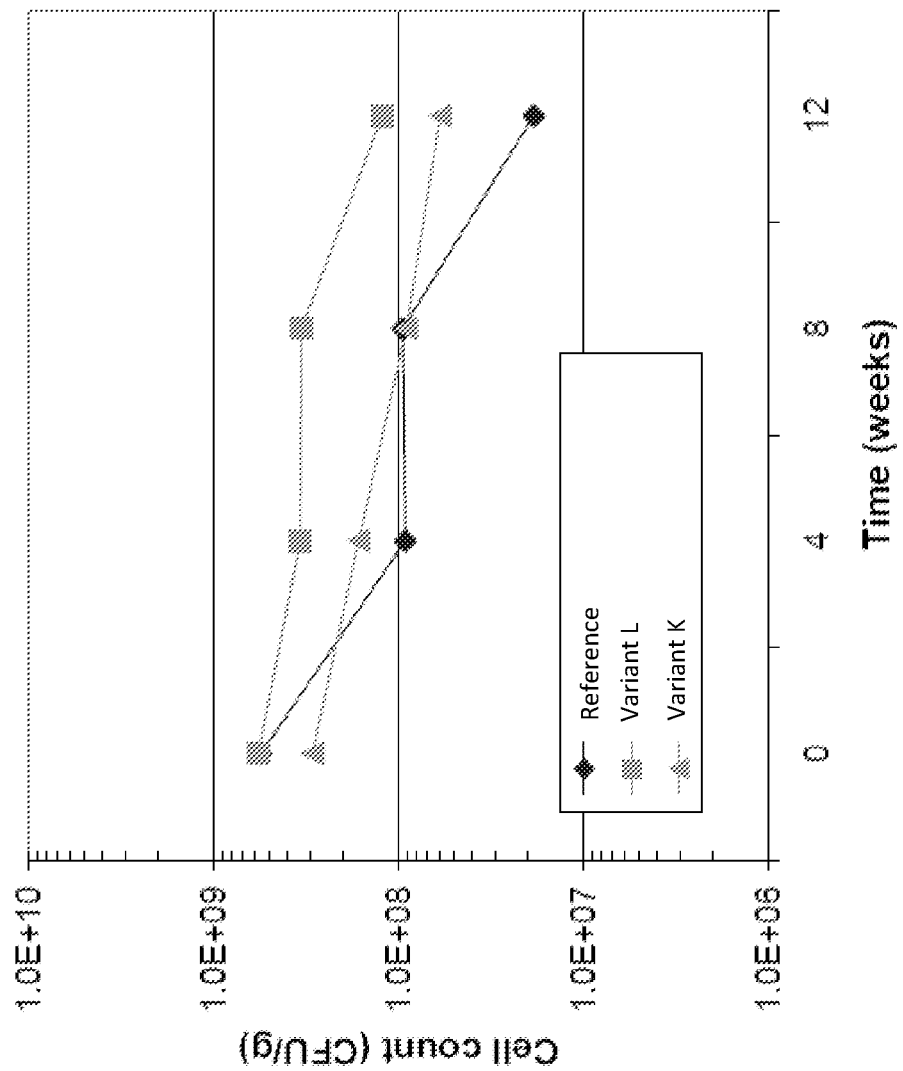

FIG. 16: Cell counts of *Lactobacillus rhamnosus* LPR after 4, 8 and 12 weeks storage in Variants K and L and in the Reference, as measured in Example 4.

Figure 17:
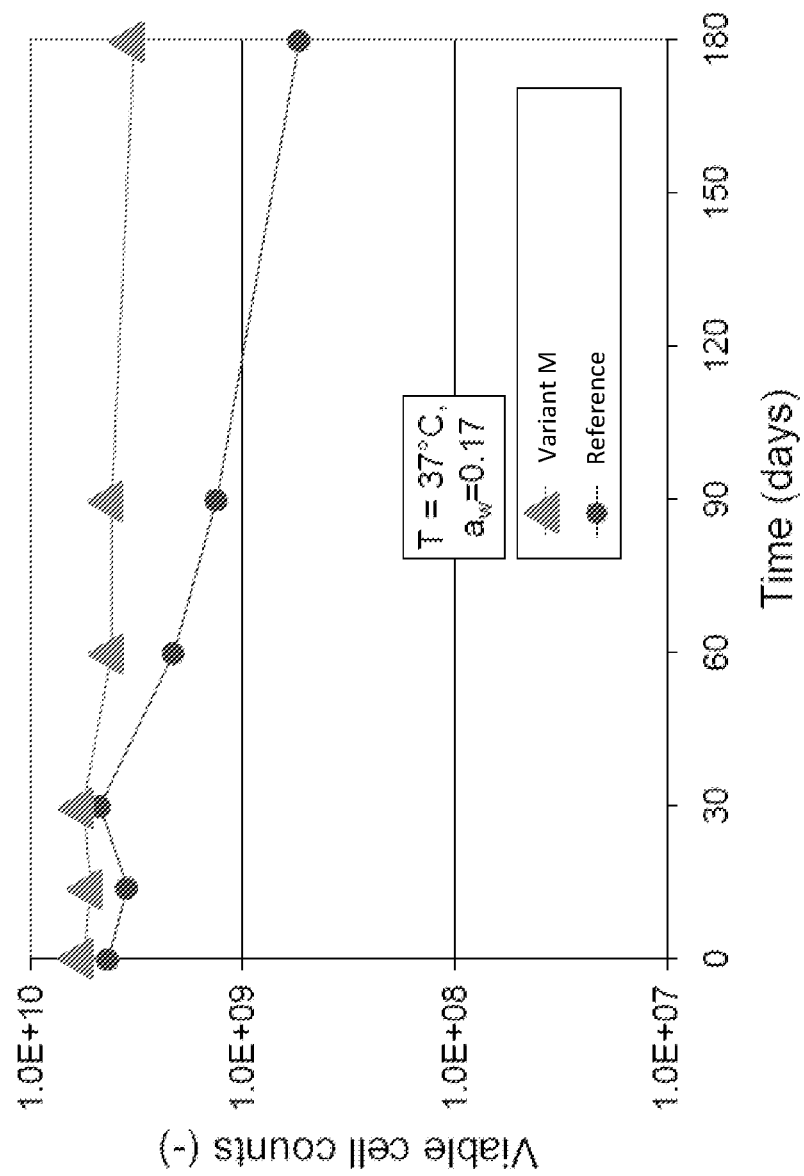

FIG. 17: Cell counts of *Bifidobacterium lactis* BL818 after 15, 30, 60, 90 and 180 days storage in Variant M and in the Reference, as measured in Example 5.

DETAILED DESCRIPTION

Definitions

"Protective agent": For the purpose of the present invention, a "protective agent" shall be understood as a composition which is effective to improve the viability of a live microorganism during drying, storage and or reconstitution.

"Drying" or "drying using warm gas": For the purpose of the present invention "drying" and "drying using warm gas" are used indistinctively and refer to any process leading to dehydration of a concentrate into a powder under the effect of a gas having a temperature higher than room temperature. The gas may be under pressure or at atmospheric pressure. Such processes are as for example spray-drying, atmospheric drying, air convective drying or fluid bed drying. In a most preferred embodiment, drying refers to spray-drying.

"Reconstitution": For the purpose of the present invention, reconstitution refers to dissolution or suspension of a powder in a liquid such as water, a specific reconstitution medium as used in analytical microbiology, or a drink like milk or juice, for example. The liquid used for reconstitution may be cold or warm. Preferably it refers to reconstitution with water.

Composition

The composition of the present invention comprises at least one carrier material comprising a polysaccharide, at least one antioxidant and at least one amino acid selected from cysteine, lysine, alanine and arginine.

Preferably the composition of the invention is not a nutritional composition, preferably it is not a complete nutritional composition, i.e. it is not a drink or a food providing balanced nutrients to fulfil the nutritional needs of a human being or animal consuming it, preferably it is not a nutritional composition constituting a whole meal for an individual consuming it.

In a preferred embodiment of the invention the composition is a protective agent. More preferably, it is a protective agent for live microorganisms, more preferably for live bacteria, most preferably for live probiotic bacteria. Even more preferably it is a protective agent for protecting live microorganisms, such as bacteria, during drying, storage and/or reconstitution. Most preferably, it is a protective agent for protecting live microorganisms during a drying process using a warm gas, such as spray-drying, during storage and/or during reconstitution.

The carrier comprises a polysaccharide. For example, the carrier can be maltodextrin, dextrin, cyclodextrin, starch, an oligosaccharide or cellulose. Preferably it is maltodextrin. For example maltodextrin having a DE of 5 to 12 can be used.

The carrier forms the bulk of the composition. It is essential to carry out a stable drying process of the composition, for example when the composition is dried with a microorganism to form a culture powder. The carrier makes it possible for example to carry out spray-drying at lower temperatures and to avoid stickiness of the powder in the spray-drying tower.

Preferably, the carrier is present in an amount of 20-60 wt %, more preferably 30-56 wt % based on the total dry weight of the composition. In an embodiment, the carrier consists of a polysaccharide as defined above.

The antioxidant can be any kind of antioxidant, such as for example vitamin C, vitamin E, glutathione, coenzyme Q10, (3-carotene, lycopene, vitamin A or a derivative thereof. Preferably, it is vitamin C or a derivative thereof, most preferably sodium ascorbate. In an embodiment, the antioxidant is not one of the amino acids cysteine, lysine, alanine and arginine, even more preferably, it is not an amino acid. The antioxidant is an essential component of the composition of the invention. When admixed with live microorganisms, it contributes to their protection during drying, storage and/or reconstitution. Preferably the antioxidant such as sodium ascorbate is present in an amount of 13-50 wt %, more prefenutritiorably 20-40 wt %, based on the total dry weight of the composition.

The composition further comprises at least one amino acid selected from cysteine, lysine, alanine and arginine. Preferably, the composition comprises a combination of at least two of the amino acids cysteine, lysine, alanine and arginine, more preferably a combination of at least three of these amino acids. In a preferred embodiment, the amino acid combination comprises lysine and/or cysteine. The amino acids are preferably in the form of their L-enantiomer (L-cysteine, L-lysine, L-alanine and L-arginine).

Preferably the amino acids altogether are present in an amount of 3.5-37 wt %, more preferably 3.5-34 wt %, most preferably 8 to 34 wt %, based on the total dry weight of the composition. Lysine, alanine and arginine are each preferably present in an amount of 0-34 wt %, more preferably 8-20 wt %, based on total dry weight of the composition. Cysteine is preferably present in an amount of 0-12 wt %, more preferably 2-10 wt %, most preferably 2-8 wt %, based on total dry weight of the composition. Using cysteine in lower concentrations than other amino acids is advantageous in that it brings a sensory benefit. In particular, limiting the concentration of cysteine to at most 10 wt %, preferably at most 8 wt %, based on the total dry weight of the composition improves the taste of the composition, leading to improved acceptability by consumers.

Particularly preferred amino acid combinations include
cysteine and alanine;
cysteine, lysine and alanine;
lysine and arginine;
cysteine and arginine;
cysteine, lysine and arginine;
lysine, alanine and arginine; and
cysteine, arginine and alanine.

The present inventors have surprisingly identified that cysteine, lysine, arginine and alanine, preferably used in the amounts described above have superior protective effects when they are used in a culture powder, thus leading to reduction of loss of live microorganisms during drying, storage and/or reconstitution of the powder.

Example 1 shows in particular that cysteine, lysine, alanine and arginine show a better protective effect compared to all other tested individual ingredients, including other amino acids such as proline, sodium glutamate or glutamine, as well as various other kinds of substances and mixtures such as sugars, sugar alcohols, proteins, gums, fibres and emulsions. Tests with combinations of ingredients in Example 1 also show that best results are obtained when these amino acids are used.

A synergistic effect is observed when amino acids are combined in the composition, in particular when cysteine and/or lysine is present. Indeed, as shown in Example 2, compositions comprising two amino acids, including lysine and/or cysteine, show better protective effect for live microorganisms during drying, storage and/or reconstitution than compositions comprising a single amino acid, at same total amino acid concentration.

The carrier material, the antioxidant and the at least one amino acid selected from lysine, cysteine, alanine and arginine are the essential components of the composition. The composition may comprise additional components. However the present inventors have discovered that improved protective effect is achieved when certain types of ingredients are used in limited concentration or even avoided. Thus it is preferred that the concentration of lactose and inositol in the composition be in the range of 0-10 wt %, based on the total dry weight of the composition. More preferably the composition is free of lactose and inositol. The present inventors have surprisingly discovered that such compositions with low lactose and inositol content has superior protective effect for live microorganisms during drying, storage and/or reconstitution. For the purpose of the present invention, "inositol" is meant as being in the form of any of its stereoisomers (myo-inositol, scyllo-inositol, muco-inositol, D-chiro-inositol, neo-inositol, L-chiro-inositol, allo-inositol, epi-inositol and cis-inositol). The most common form of inositol is myo-inositol and therefore in an embodiment inositol is defined as myo-inositol.

In a preferred embodiment, the total concentration of all the essential ingredients (carrier, antioxidant and any one or more of the amino acids lysine, cysteine, alanine and/or arginine) is comprised between 80 and 100 wt % and the total concentration of additional ingredients is comprised between 0 and 20 wt %, these percentages being defined based on the total dry weight of the composition.

In a most preferred embodiment of the invention, the composition consists essentially of at least one carrier, at least one antioxidant and at least one amino acid selected from lysine, cysteine, alanine and arginine, as defined in any of the above embodiments, preferably in the amounts indicated. More preferably the composition consists of at least one carrier, at least one antioxidant and at least one amino acid selected from lysine, cysteine, alanine and arginine, as defined in any of the above embodiments, preferably in the amounts indicated. Most preferably, it consists of maltodextrin, sodium ascorbate and at least one amino acid selected from lysine, cysteine, alanine and arginine, as defined in any of the above embodiments, preferably in the amounts indicated.

Use of the Composition

The composition according to any of the above-described embodiments can advantageously be used for the protection of live microorganisms during a drying process, such as spray-drying, storage and/or reconstitution. Preferably storage and/or reconstitution are subsequent to a drying process, preferably a spray-drying process. Preferably, the protective agent renders it possible to limit the loss of live microorganisms during a drying process and subsequent storage for a 12 weeks period at 37° C. to maximum 1.5 log, more preferably less than 1 log and to achieve a shelf life of 12 months at room temperature in a product in powder form.

The absolute log viability loss may vary depending on the microbial strain, the storage temperature, the storage time and the water activity of the medium during storage, such as for example the product in which the microorganism is incorporated. Irrespective of the absolute log viability loss measured for one particular strain, the protective effect achieved by the present invention involves a reduction of the viability log loss of that microbial strain compared to the same microbial strain dried, stored and/or reconstituted without the composition of the invention, and preferably also compared to the same microbial strain dried, stored and/or reconstituted with a protective agent consisting of the carrier and the antioxidant alone (i.e. without amino acid).

The live microorganism can be any kind of live microorganism. Preferably the microorganisms are bacteria, more preferably beneficial bacteria, such as for example probiotic bacteria. Probiotic bacteria are defined as bacterial cell preparations with a beneficial effect on the health or well-being of the host (Salminen S, Ouwehand A. Benno Y. et al. "Probiotics: how should they be defined" Trends Food Sci. Technol. 1999:10 107-10).

Microorganisms are considered as "live" when they are able to multiply under controlled culture conditions and form colonies or suspensions or when the microorganism metabolic activity and/or membrane integrity can be established using methods known to the person skilled in the art, such as for example flow cytometry.

The examples provided in the present application show that the composition of the present invention is successful in protecting diverse microbial strains during drying and subsequent storage and reconstitution. The effect is therefore not strain-specific and can be applied to a wide range of microbial strains.

Examples of bacteria which can be protected by the composition of the present invention include bifidobacteria, lactobacilli, lactococci, enterococci, streptococci, *Leuconostoc, Escherichia*, propionibacteria, or combinations thereof, preferably *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus rhamnosus, Lactobacillus johnsonii, Lactobacillus plantarum, Lactobacillus fermentum, Lactococcus lactis, Streptococcus thermophilus, Lactococcus diacetylactis, Lactococcus cremoris, Lactobacillus delbrueckii* subsp. *bulgaricus, Lactobacillus delbrueckii* subsp. *Lactis, Lactobacillus helveticus, Escherichia coli, Enterococcus faecium, Leuconostoc pseudomesenteroides, Bifidobacterium bifidum, Lactobacillus gasseri, Lactobacillus sakei, Streptococcus salivarius*, and/or mixtures thereof, as well as any of their subspecies.

Examples of bacterial strains that can efficiently be protected Include *Bifidobacterium longum* BL999 (ATCC BAA-999), *Bifidobacterium longum* (CNCM I-2618), *Bifidobacterium breve* (CNCM I-3865), *Bifidobacterium lactis* BL818 (CNCM I-3446), *Lactobacillus johnsonii* Lal (CNCM I-1225), *Lactobacillus paracasei* (CNCM I-2116), *Lactobacillus rhamnosus* LPR (CGMCC 1.3724), *Streptococcus thermophilus* (CNCM I-1422), *Streptococcus thermophilus* ST496 (CNCM I-4153), *Lactobacillus casei* (CNCM I-1518), *Lactobacillus casei* (ACA-DC 6002), *Escherichia coli* Nissle, *Lactobacillus bulgaricus* (CNCM I-1198), *Lactococcus lactis* (CNCM I-4154), or combinations thereof.

In an embodiment the microorganism is selected from *Bifidobacterium longum* BL999 (ATCC BAA-999), *Streptococcus thermophilus* ST496 (CNCM I-3915), *Lactobacillus rhamnosus* LPR (CGMCC 1.3724) and *Bifidobacterium lactis* BL818 (CNCM I-3446).

Culture Powder

The present inventors have now developed a culture powder with improved stability during storage and/or reconstitution. The culture powder comprises live microorganisms and a matrix comprising a composition as defined in any of the embodiments described above under the title "Composition". Preferably the culture powder comprises a matrix and live microorganisms, wherein the matrix consists of a composition of the invention, such as described above under the title "Composition". Most preferably, the culture powder consists of a matrix and of live microorganism, wherein the matrix comprises, or even more preferably consists of, a composition of the invention as described above under the title "Composition".

In order to ensure efficient protection of the live microorganism, the matrix:microorganism weight ratio in the culture powder is preferably of at least 1. Preferably it is comprised between 1 and 1.2 to achieve suitable protective effect while maintaining an economically effective amount of microorganisms.

Preferably the matrix is in a glassy state.

The live microorganisms are as defined above under the title "Use of the composition".

The amount of live microorganisms in the culture powder of the invention can be described as colony forming units (CFU). The required amount of live microorganisms in the culture powder can be very variable and depends on the microorganism strain and of the intended use of the powder. For example, in the case of probiotic bacteria the culture powder may comprise at least 1E+10, more preferably at least 3E+10 and most preferably at least 1E+11 CFU per gram of culture powder.

The microorganisms in the culture powder of the present invention may be in the form of a dry biomass comprising the microorganisms together with the solid content of a fermentation medium. Thus the powder may comprise a nitrogen source such as yeast extract, a carbon source such as a sugar and/or various salts suitable for use in a fermentation medium for the growth of the microorganism. It may also comprise fermented derivatives of the nitrogen and carbon source, as well as bioactive ingredients produced by the microorganisms during fermentation. Such ingredients are typically present in an amount of 0-60 wt %, preferably 0-50 wt %, based on the total dry weight of the microorganism component (biomass). Particularly low amounts of such additional ingredients are present as part of the microorganism fraction when the biomass is washed before mixing the biomass with the matrix.

The culture powder may comprise other ingredients in addition to the microorganism and the matrix. Such ingredients may typically be additional carriers, such as for example polysaccharides, disaccharides or skim milk powder. Preferably the matrix is in a glassy state, whereas the additional ingredients are not in a glassy state.

Process for Producing a Culture Powder

The first step of the process of the invention is the production of a biomass by fermentation by microorganisms. Fermentation methods, under aerobic or anaerobic conditions, are commonly known. The skilled person is able to identify suitable components of the fermentation medium and to adjust fermentation conditions based on his general knowledge, depending on the microorganism to be grown. The fermentation medium typically comprises
    a nitrogen source such as yeast extract,
    a carbon source such as a sugar
    various growth factors (e.g minerals, vitamins etc.) required by the microorganism and water.

The fermentation is preferably carried out in two steps, a starter fermentation being carried out prior to the main fermentation step. The fermentation medium can be different for the starter and the main fermentation or may be identical.

The second step of the process is the concentration of the biomass. This can also be carried out using methods known to the person skilled in the art, such as for example centrifugation or filtration. The total solid content of the biomass after concentration is preferably comprised between 10 and 35 wt %, preferably between 14 and 35 wt %, based on the total dry weight of the biomass (i.e. of the total amount of fermentation medium and produced microorganism).

Optionally, the concentration may be preceded or combined with a washing step to remove residues of the fermentation medium and/or compounds produced during fermentation. For example, washing may be performed by concentrating biomass, re-suspending the concentrated biomass in a buffer, such as a phosphate buffer, or a similar composition and re-concentrating the biomass.

The third step of the process is the conditioning of the live microorganism. During this operation, a matrix in the form of a composition of the present invention is contacted with the live microorganism. The composition of the present invention is as defined in any of the embodiments described above under the title "Composition". Preferably, said matrix is a protective agent.

The conditioning step preferably comprises the following sub-steps:

preparing an aqueous solution of the matrix, preferably having a total solid (TS) content of 40-65%, more preferably 45-60%.

adding the aqueous solution prepared in step a) to the biomass such as to achieve a matrix concentration of 40-60 wt %, preferably 50-60 wt %, most preferably 55%, based on the total dry weight of matrix and biomass (total solid content);

maintaining the biomass and the matrix into contact for a duration of 20 to 150 minutes;

adjusting the pH between 6.5 to 8.5, preferably between 6.8 to 7.2

In one alternative of the process, step c) is carried out before step d). In another alternative, step d) is carried out before step c).

The desired contact time between the biomass and the protective agents can be achieved either batch-wise or in a continuous process. When it is carried out batch-wise, the protective agents and the biomass are mixed in a batch tank and maintained under agitation for the full duration of the conditioning time, optionally under cooling conditions, preferably at T<10° C. to prevent growth of unwanted microbes and spores germination. In a continuous process, the desired contact time between biomass and protective agents can be achieved with either a continuous stirred tank reactor with a corresponding average residence time or with a plug flow reactor with a corresponding residence time (similar to a holding tube).

The conditioned biomass is then dried, using any drying method known in the art using warm gas, such as for example spray-drying, fluid bed drying, air convective drying or atmospheric drying, more preferably spray-drying. For example, the conditions described in EP0818529, which is entirely included as reference, can be applied to spray-drying process.

Optionally the dried culture powder may be dry-mixed with additional ingredients. Such ingredients may for example be additional carriers such as polysaccharides, as defined above, disaccharides or skim milk powder.

Product

The present invention also provides a product comprising the culture powder according to any of the above-described embodiments. The product can be any type of product in which the culture powder can be incorporated, such as a product in the form of a food or beverage product, an animal feed product, a nutritional supplement for human or animal, a pharmaceutical composition or a cosmetic composition. The product may be intended to be used by the final consumer in solid (such as powder form) or semi-solid form (such as for example in the form of a paste) or, alternatively, to be reconstituted into a liquid before use.

Food and beverage products include all products intended to be consumed orally by human beings, for the purpose of providing nutrition and/or pleasure. It can for example be a nutritional composition, such as for infants and/or young children, for a pregnant or lactating woman or a woman desiring to get pregnant, for individuals in need of a special nutrition due to an adverse health condition or for elderly people. More preferably, the nutritional composition is selected from infant formula, infant cereals, follow-up formula, growing-up milks and milk products for pregnant and lactating women or for women desiring to get pregnant. Other examples of food and beverage products include dairy products such as milk products or yogurts, soups, sauces, sweet and savoury snacks, powdered drinks and cereal products.

The product can also be in the form of an animal food product or a nutritional supplement for animals. Preferably, the animal is a mammal. Examples of animals include primates (e.g., humans), cows, sheep, goats, horses, dogs, cats, rabbits, rats, mice, fish, birds and the like.

Nutritional supplements are typically present in the form of a powder or of a tablet or capsule. Powder supplements typically encompass supplements to be dissolved in water or to be sprinkled on food or in a beverage. Such supplements are intended to provide additional nutrients and/or a health benefit to the subject consuming it, as well as other beneficial ingredients, such as beneficial microorganisms, for example probiotic bacteria. A supplement according to the present invention can be used for providing nutrients and/or a health benefit to human beings, as well as to animals, as defined above. Nutritional supplements include for example powder supplements to be added to breast milk, for example for premature or low birth weight infants. It also includes supplements for pregnant or lactating woman or for woman desiring to get pregnant.

Pharmaceutical products include powder, tablet or capsule products intended to treat of prevent an adverse medical condition in a subject in need thereof.

Cosmetic compositions are typically intended for an aesthetic effect on the body and may be for topical use or may be administered by oral route, in the form of a powder, tablet or capsule.

The product of the present invention preferably comprises live microorganisms, preferably beneficial bacteria, such as probiotic bacteria, in an amount of at least 5E+06 CFU per gram of product, on a dry weight basis.

The ingredients of the matrix can be selected within the above-described ingredients based on the nature of the product, for example based on taste or regulatory requirements.

The present invention will now be described in further details by the way of the following examples.

Example 1: Protective Agent for *Bifidobacterium longum* BL999 (ATCC BAA-999)

Sample Preparation

A fermentation medium suitable for the growth of *Bifidobacterium longum* BL999 was inoculated with 2% frozen-thawed bacteria. The starter was fermented under the following conditions:
10 hours fermentation time
pH-control with NaOH at pH6.

For the main fermentation, the following conditions were applied:
16 hours fermentation time,
No pH-control
Fermentation broth is covered with $CO_2$
Starter inoculation: 2%

The biomass was then concentrated by centrifugation to a total solids content (TS) of 14% (2.5E+11 CFU/g).

The centrifuged biomass was then conditioned according to the following process. The protective agent of each of the samples was dissolved in demineralised water to a total solids content of 55%. Then 300 g of centrifuged biomass were filled into a beaker, which was placed in an ice water bath. The total solids content of the biomass was measured and the protective agent solution was added at a ratio of protective agents to biomass of 55/45 (based on dry weight). The mixture was gently agitated in the ice water bath for one hour. The pH was then adjusted to pH7.

The conditioned concentrate was then spray-dried on a lab-scale spray-dryer (Buechi, B-290, Flawil, Switzerland). The air temperature was 140° C. and the tower temperature was adjusted by the concentrate flow to T=70° C. During drying, the beaker containing the concentrate was cooled in an ice water bath.

Pre-Screening

In a first round of trials, 38 ingredients were selected as potential protective agents. The effect of those ingredients on the stability of *Bifidobacterium longum* BL999 was tested by spray-drying biomass with a protective agent comprising maltodextrin DE12, sodium ascorbate and one single additional ingredient from the list of 38 compounds to be screened in the following concentrations:

TABLE 2

Composition of the protective agent for the pre-screening

| Ingredient | Concentration [wt %] |
|---|---|
| Maltodextrin DE12 | 68.2 |
| Sodium ascorbate | 13.6 |
| Individual ingredient | 18.2 |
| Total | 100 |

A control was prepared with a protective agent consisting of 13.6 wt % sodium ascorbate and 86.4 wt % maltodextrin DE12. This control was used as a reference to evaluate the effect of the protective agents on the stability of *Bifidobacterium longum* BL999 during spray-drying, storage and reconstitution.

The 38 culture powders and the control were prepared as described above, the conditioning being carried out with one of the 38 protective agents.

The cell concentration of *B. longum* in the powder was detected by classical plating methods. Such classical plating methods are summarized in the microbiology book: James Monroe Jay, Martin J. Loessner, David A. Golden. 2005. Modern food microbiology. 7th edition, Springer Science, New York, N.Y. The cells were counted in the concentrate before drying, in the culture powder directly after drying and after 2, 3, 4, 6, 8 and/or 12 weeks storage in a climatic chamber at T=37° C. above saturated potassium acetate solution ($a_w$=0.22). The cell counts after drying and after storage were determined after reconstitution of the powder with a reconstitution medium, as known by the person skilled in the art, who is well aware of the above-mentioned plating methods.

The following formulae were used for the evaluation of the data:

$$\text{Log loss} = \log\left(\frac{X_0}{X_t}\right)$$

where $X_0$ is the number of micro-organisms at time t=0 and $X_t$ the number of microorganisms at time t. When the microbiological counts were measured in k replicates, $\overline{X}_0$ is the average number of micro-organisms at time t=0 and $\overline{X}_t$ is the average number of micro-organisms at time t, the average log loss at time t is given by:

$$\text{Log loss} = \log\left(\frac{\overline{X}_0}{\overline{X}_t}\right)$$

The tested individual ingredients were selected among several groups of molecules: sugars, sugar alcohols, amino acids and proteins. All tested ingredients within a group were spray-dried on the same day and the reference was spray dried again with each group, also on the same day.

Figure 1:
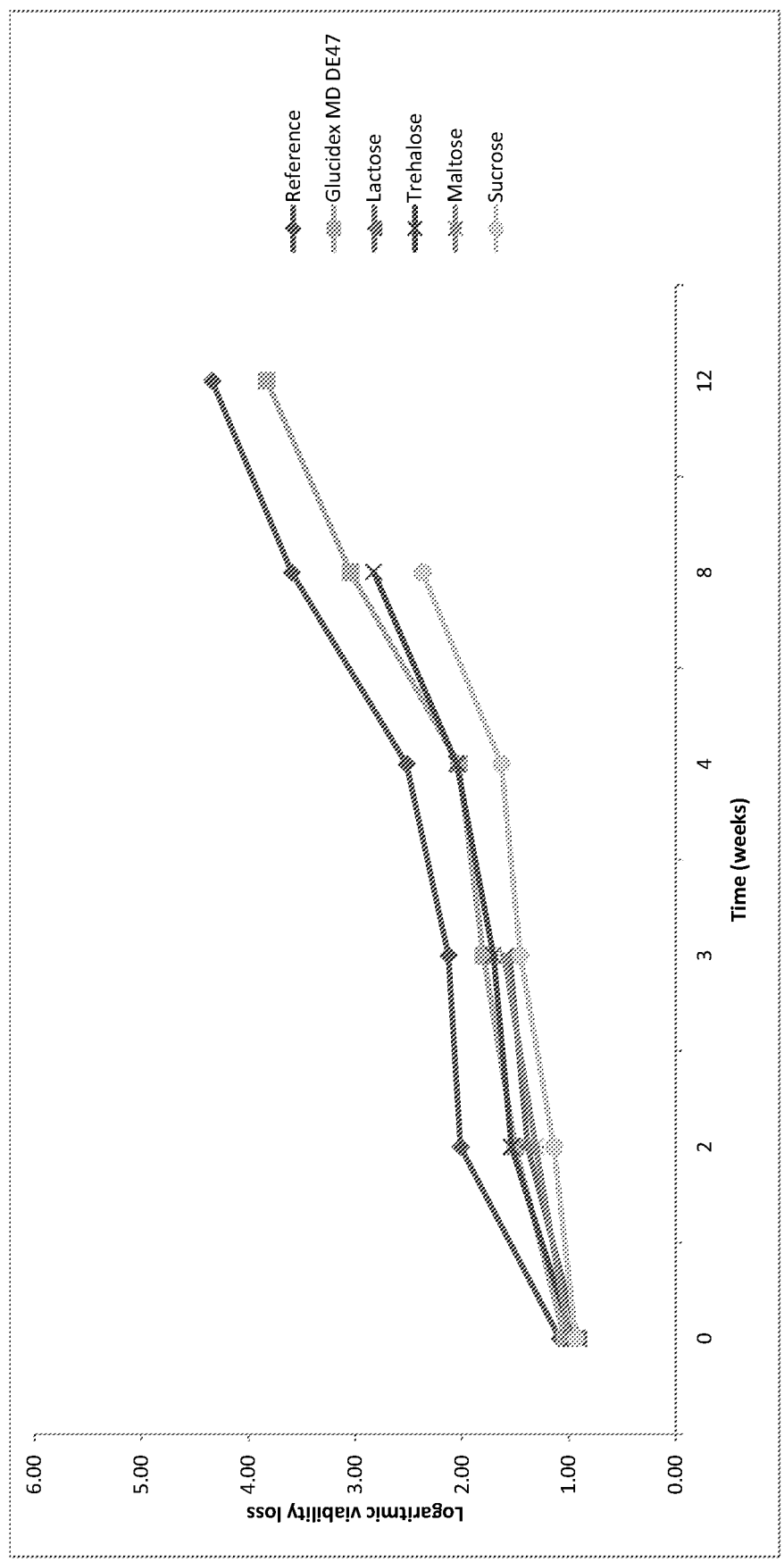
FIG. 1: Logarithmic viability loss of *Bifidobacterium longum* BL999 after spray-drying and after 2, 4, 6, 8, and 12 weeks storage with Glucidex® MD DE 47, lactose, trehalose, maltose or sucrose as protective agent, as measured in the pre-screening trial of Example 1.

The tested sugars were sucrose, maltose, trehalose, lactose and Glucidex® MD DE47. Compared to the reference, sugars did not provide any protection against the lethal stresses the bacteria experienced in the spray dryer. While the effect of the sugars on the bacterial survival during drying was minor, an impact has been observed on the storage stability. Disaccharides showed the best performance as protective agents of which sucrose proved to be the most efficient ingredient. Results are provided in FIG. 1. Sucrose and lactose were selected for the second round of tests.

The tested sugar alcohols were sorbitol, mannitol, lactitol, myo-inositol, xylitol and glycerol. Spray-drying of the concentrate with sugar alcohols proved difficult due to powder stickiness in the tower. During drying, some of the sugar alcohol showed a light protective effect such as glycerol, mannitol, xylitol and sorbitol. In the storage test, the powder samples containing glycerol collapsed after a short time. The majority of the bacteria of this variant died already after two weeks storage and the storage test was stopped. The viability loss after 8 weeks was lowest for variants containing sorbitol, mannitol, myo-inositol and lactitol. The results are shown in FIG. 2. For the second round of tests, sorbitol, lactitol and myo-inositol were selected.

The tested amino acids were L-cysteine, L-lysine, L-arginine, L-alanine, L-glutamine and sodium L-glutamate. In contrast to sugars, some amino acids stabilize the bacteria during drying. While the viability loss during drying in the reference was 1 log, only 0.2 log was lost for the variant containing cysteine. Although sodium ascorbate and cysteine are both known to have antioxidant properties, cysteine surprisingly has the ability to protect the microorganism during drying, whereas sodium ascorbate does not show significant effect on the bacterial survival during the drying process. Samples containing cysteine, lysine, arginine or alanine showed the lowest losses during storage and reconstitution, among amino acids, but also compared to all other tested ingredients in this pre-screening phase. These amino acids were selected for the second round of trials. The results are summarized in FIG. 3.

The tested proteins were gelatin, heat denatured whey protein isolate (denaturated at T=80° C. for 30 minutes), whey protein isolate and sodium caseinate. None of the proteins improved the stability during drying. During storage the heat denatured whey protein isolate showed a positive effect during the first six weeks, but after 8 weeks the viability loss was as high as for the reference. Due to their weak performance, no proteins were selected for the second round of trials. The results are summarized in FIG. 4.

All other tested ingredients showed no or very little protective activity and were not selected for the next round of trials:

gums (gum acacia, λ-carrageenan, pectin guar gum and alginate), see FIG. 5;

oligosaccharides (resistant starch, wheat fibres, raftilose and raftiline), see FIG. 6.

Other ingredients (betain HCL, carnitine) and the amino acid proline, see FIG. 7.

The pre-screening clearly shows that ingredients mentioned in the prior art as having a potential protective effect for microorganisms during drying have very variable efficiency in the protection of live microorganism in a drying process using warm gas, such as spray-drying, during storage and/or during reconstitution. The work of the present inventors has demonstrated the superior efficiency of the amino acid cysteine, lysine, alanine and arginine in combination with a carrier and an antioxidant in the protection of probiotic bacteria during spray-drying, 12 weeks subsequent storage and reconstitution.

Trials with Combinations of Ingredients

After having selected the most promising ingredients in the pre-screening step, an experimental design was set up to find out the best protective agents mixes and the optimal concentration profiles.

First, feasibility trials were performed where constraints regarding the processing were defined.

The concentration of amino acids altogether had to be limited to a total of 36.5 wt %, based on the total dry weight of the protective agent. Spray-drying became almost impossible at higher concentrations of amino acids, due to powder stickiness.

For a stable spray-drying process, a minimum amount of 31 wt % of maltodextrin, based on the total dry weight of the protective agent mix, had to be incorporated into the protective agent mix.

The content of biomass was fixed to 45 wt % in the final powder and thus the protective agent amounted to 55 wt %, based on the total dry weight of the biomass and protective agent.

The experimental design comprised 32 variants consisting of various combinations of the ingredients identified as promising protective agents in the pre-screening trial. Due to capacity of the spray-drier, these variants were divided into groups of 5 variants and a Reference, each group being spray-dried in a single day. As Reference a protective agent mix previously identified as having some weak protective effect on microorganism during spray-drying was used. The composition of the Reference is provided in Table 3 below. In addition to the 5 variants, the Reference was spray-dried on each trial day as well. The Reference was always spray-dried on a different position in the setup of a trial day to eliminate effects coming from different storage times of the biomass. The viability loss measurement was measured after all samples of the group had been spray-dried. Therefore the storage time before the measurement carried out after spray-drying varied from 0 to 6 hours due to the time needed to spray dry the 5 variants and the Reference.

TABLE 3

| Composition of the Reference | |
| --- | --- |
| Ingredient | Concentration [wt %] |
| Maltodextrin | 50 |
| Lactose | 20 |
| Myo-inositol | 9 |
| Sodium glutamate | 7 |
| Sodium ascorbate | 14 |
| Total | 100 |

All variants were prepared as described for the pre-screening trial, using the combination of ingredients instead of the single ingredient. They were then spray-dried, stored after drying for 12 weeks and analysed after 2, 4, 6, 8 and 12 weeks, as described above with respect to the pre-screening trials. The same mathematical formulae were used for the data analysis. The results of the two groups including the most promising variants are provided as FIGS. 9 and 10. The compositions of the variants included in these trials are provided in Table 4 below.

TABLE 4

| | | | | | | | | | | | | | |
| --- | --- | --- | --- | --- | --- | --- | --- | --- | --- | --- | --- | --- | --- |
| Composition of variants A to H | | | | | | | | | | | | | |
| Variant | Maltodextrin | Sodium ascorbate | Sorbitol | Myo-inositol | Lactose | Sucrose | Lactitol | L-Lysine | L-cysteine hydro-cloride | L-arginine | L-alanine | Sodium glutamate | |
| Ref | 50.0 | 14.0 | 0.0 | 9.0 | 20.0 | 0.0 | 0.0 | 0.0 | 0.0 | 0.0 | 0.0 | 7.0 | Comparative |
| A | 31.8 | 13.6 | 9.1 | 9.1 | 0.0 | 0.0 | 0.0 | 0.0 | 12.2 | 12.2 | 12.2 | 0.0 | Invention |
| B | 31.8 | 13.6 | 9.1 | 9.1 | 0.0 | 0.0 | 36.4 | 0.0 | 0.0 | 0.0 | 0.0 | 0.0 | Comparative |
| C | 43.8 | 36.4 | 0.0 | 4.0 | 0.0 | 0.0 | 8.0 | 2.7 | 2.7 | 2.7 | 0.0 | 0.0 | Invention |
| D | 31.8 | 34.55 | 0.0 | 0.0 | 0.0 | 0.0 | 0.0 | 11.3 | 11.3 | 0.0 | 11.3 | 0.0 | Invention |
| E | 31.8 | 34.6 | 0.0 | 0.0 | 11.3 | 11.3 | 11.3 | 0.0 | 0.0 | 0.0 | 0.0 | 0.0 | Comparative |
| F | 31.8 | 26.6 | 0.0 | 0.0 | 0.0 | 0.0 | 20.7 | 0 | 6.9 | 6.9 | 6.9 | 0.0 | Invention |

TABLE 4-continued

Composition of variants A to H

| Variant | Maltodextrin | Sodium ascorbate | Sorbitol | Myo-inositol | Lactose | Sucrose | Lactitol | L-Lysine | L-cysteine hydro-cloride | L-arginine | L-alanine | Sodium glutamate | |
|---|---|---|---|---|---|---|---|---|---|---|---|---|---|
| G | 37.6 | 36.4 | 9.1 | 9.1 | 0.0 | 3.8 | 0.0 | 1.3 | 1.3 | 0.0 | 1.3 | 0.0 | Invention |
| H | 31.8 | 29.6 | 0.0 | 12.9 | 25.6 | 0.0 | 0.0 | 0.0 | 0.0 | 0.0 | 0.0 | 0.0 | Comparative |

The results depicted in FIG. 9 show that Variant B and the Reference, which do not contain any of the amino acids lysine, cysteine, arginine and/or alanine required in the present invention have a much weaker protective effect, as the logarithmic viability loss for these two samples is much higher than for the variants of the invention. The best performing variant in this design of experiment is Variant D, having three amino acids and being free of other ingredients (i.e. it consists of sodium glutamate, maltodextrin, and the amino acids lysine, cysteine and alanine). On FIG. 10, variants F and G according to the invention also show much better protective effect than Variants E and H (having no amino acid).

This example shows that the protective effect is provided with protective agents comprising diverse mixtures of the amino acids cysteine, lysine, alanine and arginine, in a broad range of total concentrations, ranging from 3.8 to 36.5 wt %, based on the total dry weight of the protective agent.

Example 2: Comparison of Diverse Amino Acids Ratios

Samples of culture powder were prepared comprising *Bifidobacterium longum* BL999 (ATCC BAA-999) and a matrix comprising maltodextrin, sodium ascorbate and the amino acids cysteine, lysine, alanine and arginine alone or in combinations by pairs, as described in Table 5 below.

TABLE 5

Amino acid composition in the matrix of tested samples

| Sample no. | Lysine (%) | Arginine (%) | Cysteine (%) | Alanine (%) |
|---|---|---|---|---|
| 1 | 34 | 0 | 0 | 0 |
| 2 | 0 | 34 | 0 | 0 |
| 3 | 0 | 0 | 34 | 0 |
| 4 | 0 | 0 | 0 | 34 |
| 5 | 17 | 17 | 0 | 0 |
| 6 | 17 | 0 | 17 | 0 |
| 7 | 17 | 0 | 0 | 17 |
| 8 | 0 | 17 | 17 | 0 |
| 9 | 0 | 17 | 0 | 17 |
| 10 | 0 | 0 | 17 | 17 |

All percentages are defined by weight, relative to the total weight of the matrix.

The samples were prepared with 55% matrix and 45% of *Bifidobacterium longum* BL999 (ATCC BAA-999), the percentage being defined by weight, based on the total dry weight of the culture powder. The matrix consisted of 33% maltodextrin DEX, 33% sodium ascorbate and 34% of amino acid composition as described in Table 5, the percentages being defined by weight relative to the total weight of the matrix.

The samples were prepared as follows. *B. longum* BL999 was grown for 16 h at 37° C. in a 7-L fermenter (new MBR, CH-Zürich) under CO2-headspace atmosphere using the same fermentation medium as in Example 1. The pH of the fermentation was not controlled. Cell suspension collected from the fermenter was centrifuged at 4500 rpm for 20 min at 5° C. (Sorvall RC3C Plus). After discarding the supernatant, the biomass was stored at 4° C. prior to mixing with the protective matrix. The pH of the concentrate was adjusted to 7.0 by drop-wise addition of 30% NaOH before drying with analytical convective dryer (ACD) at lab scale (built by IVV-Fraunhofer Institut, DE-Freising). Relevant drying parameters such as air humidity, air temperature and air flow rate were adjusted as follows:

Air flow: 40 m$^3$/h
Temperature of the drying air: 60° C.
Relative humidity of drying air 8%
Duration 660 s The log loss was analyzed for each sample as described in Example 1, after drying, and after 8 weeks storage above saturated sodium acetate solution ($a_w$=0.22) in a climatic chamber at T=37° C. The cell concentration of *B. longum* BL999 was measured before drying and after 8 weeks storage using the method described in Example 1. The log loss was also calculated using the equations described in Example 1.

The results are provided in FIGS. 11 to 14. These figures show that samples in which a pair of amino acids was used in the protective agent exhibited reduced log viability loss compared to samples where only one amino acid was used. The only exception is the sample produced with a combination of the two amino acids alanine and arginine, which showed increased viability loss compared to arginine or alanine alone. Even though the effect of the combination of alanine and arginine proved to be lower than that of the individual ingredients, the results provided evidence of significant protective effect of alanine and arginine as single ingredients or combined in a pair.

These results provide evidence of a synergy between the amino acids when used in pairs, in particular when cysteine and/or lysine is present, compared to the use as single amino acid, because at same concentrations, pairs of amino acids provide better stabilization than single amino acids.

Example 3: Protective Agent for *Streptococcus thermophilus* ST496 (CNCM I-3915)

A comparative experiment has been performed to evaluate the performance of a composition according to the invention for the protection of the microorganism *Streptococcus thermophilus* ST496 (CNCM I-3915) during storage and reconstitution.

A Reference and two samples (Variants I and J) were prepared. As Reference a protective agent mix previously identified as having some weak protective effect on microorganism during spray-drying was used. The composition of the Reference is provided in Table 3 above. The protective agent composition used in each test sample is given in Table 6 below. For all samples the matrix concentration was of 55 wt % and the microorganism concentration was of 45 wt %, based on total solids.

TABLE 6

Composition of samples I and J

| Ingredient | Variant I | Variant J |
|---|---|---|
| Maltodextrin DE6 | 55.00 | 50.00 |
| Sodium ascorbate | 22.32 | 25.00 |
| L-Lysine HCL | 9.34 | 10.30 |
| L-Cysteine HCL monohydrate | 4.00 | 4.40 |
| L-Alanine | 9.34 | 10.30 |
| Total | 100.00 | 100.00 |

The Reference and test samples were all prepared using the same method, as follows. *S. thermophilus* was produced in 3000 L bioreactor at 40° C. for 9 h at pH constant after inoculation of a suitable medium containing nitrogen source, carbon source and trace elements at 2% with the starter culture. Biomass at end of fermentation was concentrated by centrifugation and conditioned with the matrix for 1 h. Biomass and matrix after conditioning and pH adjustment at 7 were spray-dried at large scale using a spray drying tower size wise close to an industrial scale drying tower.

After spray-drying, the Reference and test samples were subjected to an accelerated storage test. The culture powder was mixed with skim milk powder at a ratio of 1 to 100, after spray-drying of the culture powder. Then this mixture was stored at 37° C. and $a_w$=0.25 for 12 weeks. The cell counts were measured in the Reference and in the test samples immediately after spray-drying and after 4, 8 and 12 weeks storage. The cell counts were measured as described in Example 1.

The results are shown in FIG. 15. It can be seen from the graph that the total microorganism cell counts are significantly higher after 12 weeks storage and reconstitution in Variants I and J (according to the invention), than in the Reference. This shows that the composition of the invention is effective in protecting live *Streptococcus thermophilus* ST456 during storage and reconstitution after spray-drying. When combining this observation with what is obtained in the other examples, it shows that the protective effect of the composition of the invention is not strain specific and is effective on a large variety of microorganism strains. In addition, the effect is achieved with different concentrations of the ingredients of the protective composition. This example also shows that the protective effect is obtained when the culture powder is produced at large scale.

Example 4: Protective Agent for *Lactobacillus rhamnosus* LPR (Deposited as CGMCC 1.3724)

A comparative experiment has been performed to evaluate the performance of a composition according to the invention for the protection of the microorganism *Lactobacillus rhamnosus* LPR (deposited as CGMCC 1.3724) during spray-drying, storage and reconstitution.

A Reference and two samples (Variants K and L) were prepared. As Reference a protective agent mix previously identified as having some weak protective effect on microorganism during spray-drying was used. The Reference composition is provided in Table 3 above. The protective agent composition used in each test sample is given in Table 7 below. For all samples the matrix concentration was of 55 wt % and the microorganism concentration was of 45 wt %, based on total solids.

TABLE 7

Composition of samples K and L

| Ingredient | Variant I | Variant J |
|---|---|---|
| Maltodextrin DE6 | 60.00 | 55.00 |
| Sodium ascorbate | 19.85 | 22.32 |
| L-Lysine HCL | 8.30 | 9.34 |
| L-Cysteine HCL monohydrate | 3.55 | 4.00 |
| L-Alanine | 8.30 | 9.34 |
| Total | 100.00 | 100.00 |

The Reference and test samples were all prepared using the same method, as follows.

*L. rhamnosus* was produced in 3000 L bioreactor at 37° C. for 16 h at pH constant after inoculation of a suitable medium containing nitrogen source, carbon source and trace elements was used to obtain high yield at 4% with the starter culture. Biomass at end of fermentation was concentrated by centrifugation and conditioned with the matrix for 1 h. Biomass and matrix after conditioning and pH adjustment at 7 were spray-dried at large scale using a spray drying tower size wise close to industrial scale drying tower.

After spray-drying, the Reference and test samples were subjected to an accelerated storage test. The culture powder was mixed with skim milk powder at a ratio of 1 to 100, after spray-drying of the culture powder. Then this mixture was stored at 37° C. and $a_w$=0.24 for 12 weeks. The cell counts were measured in the Reference and in the test samples immediately after spray-drying and after 4, 8 and 12 weeks storage. The cell counts were measured as described in Example 1.

The results are shown in FIG. 16. It can be seen from the graph that the total microorganism cell counts are significantly higher after 12 weeks storage and reconstitution in Variants K and L (according to the invention), than in the Reference. This shows that the composition of the invention is effective in protecting live *Lactobacillus rhamnosus* LPR during storage and reconstitution after spray-drying. When combining this observation with what is obtained in the other examples, it shows that the protective effect of the composition of the invention is not strain specific and is effective on a large variety of microorganism strains. In addition, the effect is achieved with different concentrations of the ingredients of the protective composition. This example also shows that the protective effect is obtained when the culture powder is produced at large scale.

Example 5: Protective Agent for *Bifidobacterium lactis* BL818 (Deposited as CNCM I-3446)

A comparative experiment has been performed to evaluate the performance of a composition according to the invention for the protection of the microorganism *Bifidobacterium lactis* BL818 (deposited as CNCM I-3446) during spray-drying, storage and reconstitution.

A Reference and one test sample (Variant M) were prepared. As Reference a protective agent mix previously identified as having some weak protective effect on microorganism during spray-drying was used. The composition of the Reference is provided in Table 3 above. The protective agent composition used in the test sample is given in Table 8 below. For all samples the matrix concentration was of 55 wt % and the microorganism concentration was of 45 wt %, based on total solids.

TABLE 8

Composition of samples M

| Ingredient | Variant M |
|---|---|
| Maltodextrin DE6 | 52.00 |
| Sodium ascorbate | 23.80 |
| L-Lysine HCL | 10.00 |
| L-Cysteine HCL | 4.20 |
| L-Alanine | 10.00 |
| Total | 100.00 |

The Reference and the test sample were prepared using the same method.

After spray-drying, the Reference and the test sample were subjected to an accelerated storage test at 37° C. and $a_w$=0.17 for 180 days. The cell counts were measured in the Reference and in the test sample immediately after spray-drying and after 15, 30, 60, 90 and 180 days storage. The cell counts were measured as described in Example 1.

The results are shown in FIG. 17. It can be seen from the graph that the total microorganism cell count is significantly higher after 180 days storage and reconstitution in Variants M (according to the invention), than in the Reference. This shows that the composition of the invention is effective in protecting live *Bifidobacterium lactis* BL818 during storage and reconstitution after spray-drying. The log viability loss (calculated as described in Example 1) is of only 0.24 after 180 days in the sample of the invention, showing a very efficient protective effect.

When combining this observation with what is obtained in the other examples, this example shows that the protective effect of the composition of the invention is not strain specific and is effective on a large variety of microorganism strains. In addition, the effect is achieved with different concentrations of the ingredients of the protective composition. This example also shows that the protective effect is obtained when the culture powder is produced at large scale.

The invention is claimed as follows:

1. A composition comprising a carrier material comprising a polysaccharide, the composition further comprising at least one antioxidant and at least one amino acid selected from the group consisting of (i) cysteine and alanine; (ii) cysteine, lysine, and alanine; (iii) lysine and arginine; (iv) cysteine and arginine; (v) cysteine, lysine, and arginine; (vi) lysine, alanine, and arginine; and (vii) cysteine, arginine, and alanine.

2. The composition according to claim 1, wherein the carrier material is selected from the group consisting of maltodextrin, dextrin, cyclodextrin, starch, an oligosaccharide and cellulose.

3. The composition according to claim 1, wherein the at least one antioxidant is selected from the group consisting of vitamin C, vitamin E, glutathione, coenzyme Q10, B-carotene, lycopene, vitamin A and a derivative thereof.

4. The composition according to claim 1, wherein a total of the at least one amino acid is 3.5 wt. % to 36.5 wt. % of the total dry weight of the composition.

5. The composition according to claim 1, wherein:
the carrier is 20-60 wt. %;
the at least one antioxidant is 13-50 wt. %;
any cysteine is no greater than 12 wt. %;
any lysine is no greater than 34 wt. %;
any arginine is no greater than 34 wt. %; and
any alanine is no greater than 34 wt. %;
all percentages defined by weight based on the total dry weight of the composition.

6. The composition according to claim 1 consisting essentially of the polysaccharide, the at least one antioxidant and the at least one amino acid.

7. A culture powder comprising live microorganisms and a matrix comprising the composition of claim 1, wherein a dry weight ratio of the matrix to the live microorganisms is at least 1.

8. The culture powder according to claim 7, wherein the live microorganisms are bacteria.

9. The culture powder according to claim 8, wherein the bacteria is selected from the group consisting of bifidobacteria, lactobacilli, lactococci, enterococci, streptococci, *Leuconostoc, Escherichia*, propionibacteria, and combinations thereof.

10. A product comprising a culture powder according to claim 7, wherein the product is selected from the group consisting of a nutritional composition, a food or beverage product, an animal feed product, a food supplement, a pharmaceutical composition and a cosmetic composition.

11. The composition according to claim 1, wherein any lysine is 8 to 20% of the composition based on dry weight, any alanine is 8 to 20% of the composition based on dry weight, any arginine is 8 to 20% of the composition based on dry weight, and any cysteine is 2 to 10% of the composition based on dry weight.

* * * * *